US012751912B2

(12) United States Patent
De Tollenaere et al.

(10) Patent No.: US 12,751,912 B2
(45) Date of Patent: Oct. 6, 2026

(54) *MANGIFERA INDICA* LEAVES EXTRACTS

(71) Applicant: Givaudan SA, Vernier (CH)

(72) Inventors: Morgane De Tollenaere, Reims (FR); Cyrille Jarrin, Muret (FR); Carole Lambert, Grepiac (FR); Romain Reynaud, Toulouse (FR); Amandine Scandolera, Sault-Saint-Remy (FR); Bénédicte Sennelier Portet, Jonquerettes (FR)

(73) Assignee: GIVAUDAN SA, Vernier (CH)

( * ) Notice: Subject to any disclaimer, the term of this patent is extended or adjusted under 35 U.S.C. 154(b) by 563 days.

(21) Appl. No.: 18/033,010

(22) PCT Filed: Oct. 27, 2021

(86) PCT No.: PCT/EP2021/079845

§ 371 (c)(1),
(2) Date: Apr. 20, 2023

(87) PCT Pub. No.: WO2022/090322

PCT Pub. Date: May 5, 2022

(65) Prior Publication Data

US 2025/0352458 A1 Nov. 20, 2025

(30) Foreign Application Priority Data

Oct. 28, 2020 (GB) .................................... 2017114

(51) Int. Cl.
*A61K 36/00* (2006.01)
*A61K 8/9789* (2017.01)
*A61Q 5/00* (2006.01)
*A61Q 19/00* (2006.01)

(52) U.S. Cl.
CPC .............. *A61K 8/9789* (2017.08); *A61Q 5/00* (2013.01); *A61Q 19/00* (2013.01); *A61Q 19/007* (2013.01)

(58) Field of Classification Search
CPC ..................................................... A61Q 19/00
See application file for complete search history.

(56) References Cited

U.S. PATENT DOCUMENTS

| | | | | |
|---|---|---|---|---|
| 9,370,541 | B2 | 6/2016 | Msika et al. | |
| 2012/0202755 | A1 | 8/2012 | Wang et al. | |
| 2018/0116936 | A1 * | 5/2018 | Pan | A61K 8/602 |

FOREIGN PATENT DOCUMENTS

| | | | | |
|---|---|---|---|---|
| CN | 101647794 | A | 2/2010 | |
| CN | 106913 487 | A | 7/2017 | |
| FR | 3073525 | A1 * | 5/2019 | C07C 403/24 |
| JP | 2006298814 | A | 11/2006 | |

OTHER PUBLICATIONS

Jacqueline C. Barreto, et al., "Characterization and Quantitation of Polyphenolic Compounds in Bark, Kernel, Leaves, and Peel of Mango ( *Mangifera indica* L.)", Journal of Agricultural and Food Chemistry, Jul. 1, 2008, vol. 56, No. 14.
Mintel GNPD (mintel.com), "Double Serum Complete Age Control Concentrate", Feb. 11, 2020, Database accession No. 7261683.
Mintel GNPD (mintel.com), "Bright Micro Solution Cleanser", Mar. 12, 2020, Database accession No. 7430175.
Mintel GNPD (mintel.com), "Body Cream", Feb. 2018, Record ID 5431991.
Mintel GNPD (mintel.com), "Hand Cream", Mar. 2019, Record ID 6418249.
International Search Report for PCT Application No. PCT/EP2021/079845, mailed on Feb. 14, 2022.
Great Britain Search Report for Application No. GB2017114.6, dated on Mar. 18, 2021.
Savarnikarana Lepa, Key Attributes of TKDL—RS23/1720A—Title of Traditional Knowledge Resource.
Tila Anba Musawwide-e-sha,r, Key Attributes of TKDL—MH3/214A—Title of Traditional Knowledge Resource.

* cited by examiner

*Primary Examiner* — Qiuwen Mi
(74) *Attorney, Agent, or Firm* — Curatolo Sidoti & Trillis Co., LPA; Floyd Trillis, III; Salvatore A. Sidoti

(57) ABSTRACT

The invention is related to an extract of *Mangifera indica* leaves provided in a mixture of propanediol and water as carrier solvent, to its use in cosmetic applications and to cosmetic compositions comprising the extract.

21 Claims, 20 Drawing Sheets

Specification includes a Sequence Listing.

Evolution of ratio SQOOH/SQ (%)

Wilcoxon matched-pairs signed test vs D0
Mann Whitney test vs placebo

Binding energy = -164.035 +/- 1.011 kJ/mol

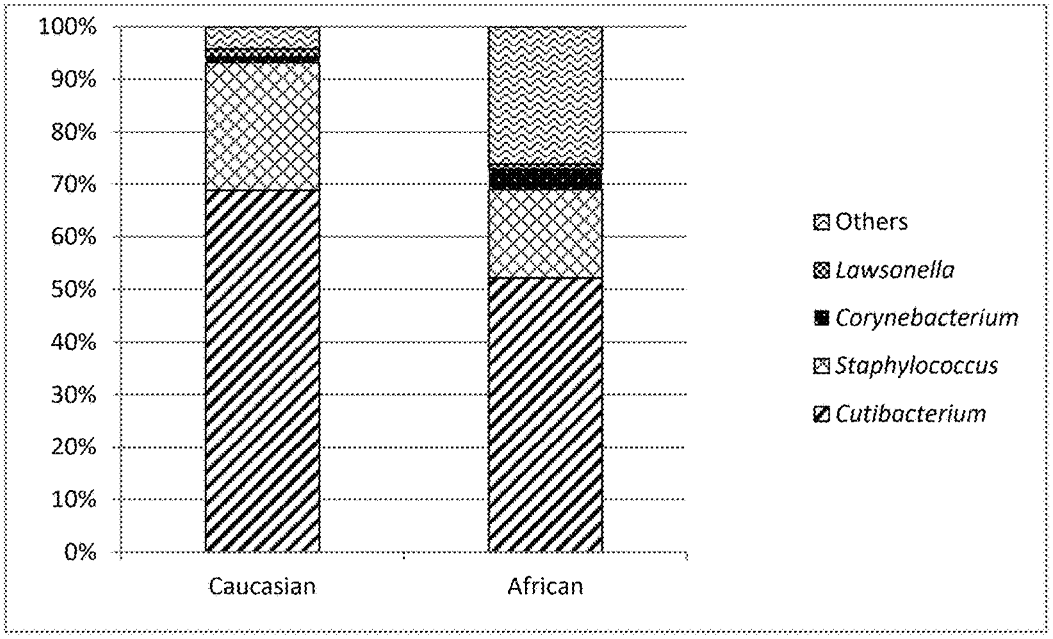

Figure 25

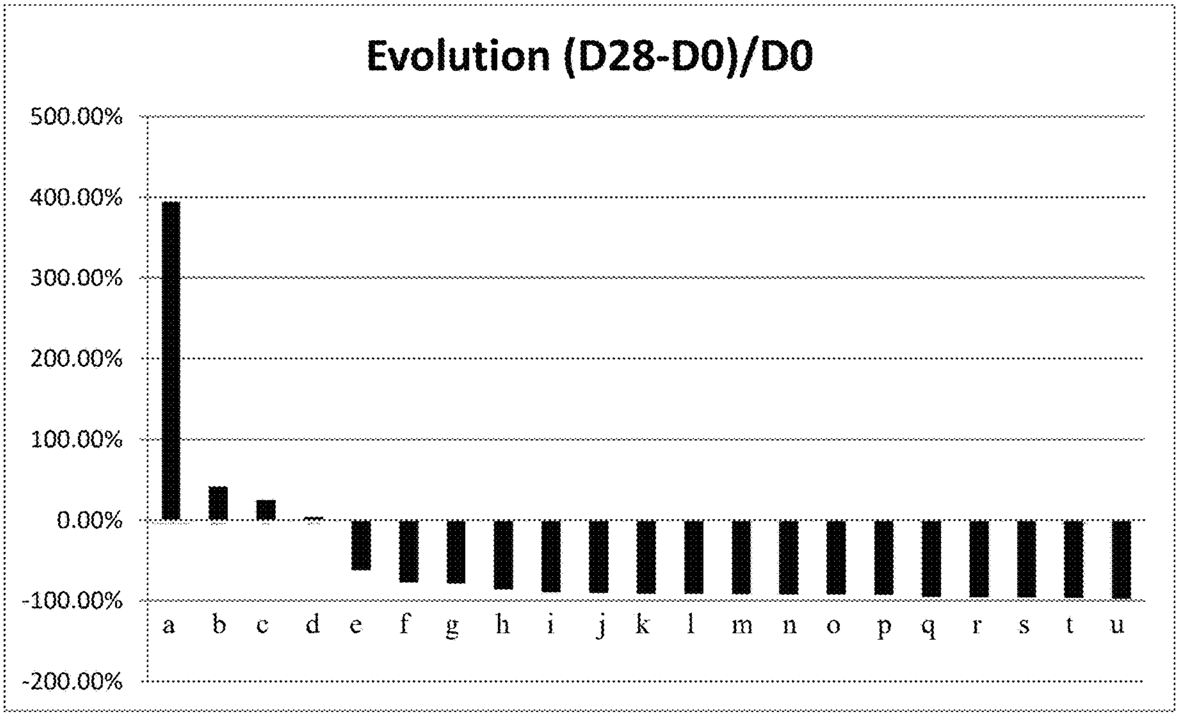

Figure 26: a) Methylobacterium-Methylorubrum, b) Sphingomonas, c) Kingella, d) Leptotrichia, e) Moraxella, f) Paracoccus, g) Ornithinimicrobium, h) Rubellimicrobium, i) Marmoricola, j) Pseudonocardia, k) Noviherbaspirillum, l) Nocardioides, m) Deinococcus, n) Blastococcus, o) Microvirga, p) Flavisolibacter, q) Modestobacter, r) Rubrobacter, s) Solirubrobacter, t) Craurococcus-Caldovatus, u) Hymenobacter

SEQUENCE LISTING

```
<160> NUMBER OF SEQ ID NOS: 2

<210> SEQ ID NO 1
<211> LENGTH: 17
```

-continued

```
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (9)..(9)
<223> OTHER INFORMATION: n is a, c, g, or t

<400> SEQUENCE: 1

cctacgggng gcwgcag                                              17


<210> SEQ ID NO 2
<211> LENGTH: 21
<212> TYPE: DNA
<213> ORGANISM: Artificial Sequence
<220> FEATURE:
<223> OTHER INFORMATION: synthetic construct

<400> SEQUENCE: 2

gactachvgg gtatctaatc c                                         21
```

*MANGIFERA INDICA* LEAVES EXTRACTS

The present invention relates to an extract of *Mangifera indica* leaves and to methods to make said extract. It further relates to cosmetic compositions comprising the extract of *Mangifera indica* leaves.

*Mangifera indica*, commonly known as Mango, belongs to the family of Anacardiaceae. The genus *Mangifera* consists of about 30 species of tropical trees in the flowering plant family. *M. indica* has a long history of home use as an herbal remedy in ethnopharmacology since ancient times. The plant and its fruits are also referred to vernacular names including manga, mangueira, skin mango in Brazil; mangguo in China; Aamin in Fiji; embe, mwembe in Kenya and Tanzania, and bowen mango in United States. Native from Southern Asia, especially Eastern India, *M. indica* has been largely cultivated and introduced in West Africa and Brazil in the early 16th Century. Now this tree can be found in most tropical biotopes in India, Africa, Southeast Asia, Malaysia and Australia.

Mango fruits are widely used as food, and play an important role in the diet of some populations. But also other parts of the plant like wood, bark, roots or leaves could be of use, for example as construction material or as a source of dyes. Fruit extracts, typically provided as glycerinic-aqueous extracts, are also used in cosmetic applications.

It is an aim of the present invention to add value to the leaves of *Mangifera indica*. They are renewable parts of the plant and are not in competition for other essential purposes like nutrition in case of the fruits. The timing of harvesting the leaves can be chosen to not affect the production of the fruits.

This is achieved by the extract of the present invention.

REFERENCE TO ELECTRONIC SEQUENCE LISTING

The contents of the electronic sequence listing (31066US_ST25); Size: 683 bytes; Date of Creation: May 18, 2026) is herein incorporated by reference in its entirety.

BRIEF DESCRIPTION OF THE DRAWINGS

FIG. 25 shows that at the genus level, African skins present the same major genera as Caucasian skin: the *Cutibacterium* and *Staphylococcus* genera.

FIG. 26 summarizes the evolution of the genera in Table 16 impacted by the application of the placebo during 28 days on African skins.

Figure 1:
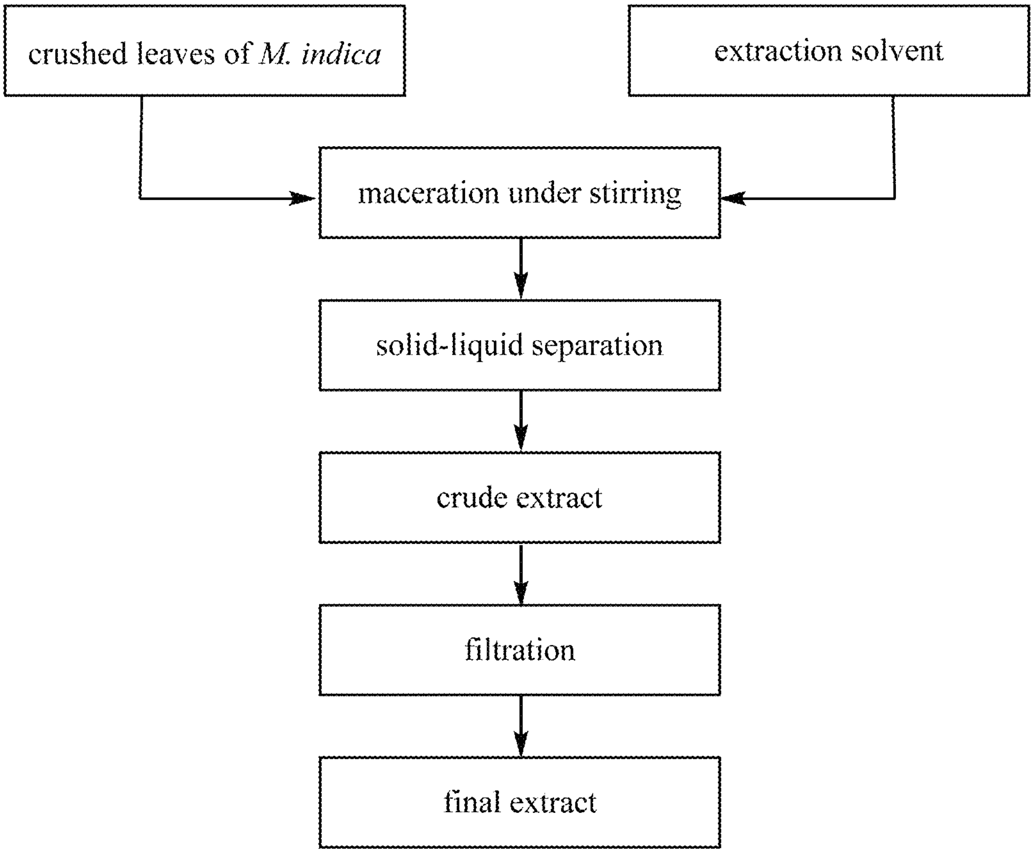
FIG. 1 is a general extraction scheme using crushed leaves of *M. indica.*

In a first aspect, the present invention provides an extract of *Mangifera indica* leaves provided in a mixture of propanediol and water as carrier solvent. Said extract is useful for compositions and methods for skin treatment. In particular, they are cosmetic, non-therapeutic compositions and methods.

Propanediol is also known as propane-1.3-diol. It is a solvent that can be provided from natural origins, representing a green, bio-based solvent, which is COSMOS approved. It is commonly used in topical applications and cosmetics.

When used as carrier solvent for the extract of *Mangifera indica* leaves, the mixture of propanediol and water is stabilizing the product against alteration by microbial growth, and no addition of preservatives is necessary. The *Mangifera indica* extract of the present invention is fully natural origin and from renewable sources.

In a further aspect of the present invention, the extract of *Mangifera indica* leaves is provided, wherein the mixture of propanediol and water is used as extraction solvent.

The choice of the extraction solvent might have impact on the composition and properties of the extract. When using a mixture of propanediol and water as extraction solvent, the obtained extract does have a high level of active compounds like Mangiferin and others. At the same time, the extract is less coloured in comparison with extracts obtained from extractions with alternative solvents, like for example ethanol or glycerol. However, an intensive coloration of the extract is not always desired, as it can cause limitation in its use, and should therefore be avoided, if possible.

The observed coloration might be caused by extraction of further ingredients from the leaves. For example, by ethanolic extraction, also chlorophyll is removed from the leaves. Apparently this is less the case when using the mixture of propanediol and water as extraction solvent.

Furthermore, the use of a mixture of propanediol and water as extraction solvent does also provide a safety advantage, when compared to ethanolic extractions, which require the use of capabilities in accordance with ATEX directive (which describes the minimum safety requirements of the workplace and equipment used in explosive atmosphere). Such safety measures are not required for extractions with propanediol—water mixtures.

Alternatively, there is provided an extract of *Mangifera indica* leaves extracted by solvents or solvent mixtures like ethanol, ethanol/water or glycerol.

Such extracts also contain significant levels of active compounds like Mangiferin and others. They might show a significant coloration. For example, an ethanolic (EtOH 75% in water) extract of *Mangifera indica* leaves is green. Such an extract can be still used in applications in which its coloration does not matter, for example when it is admixed into a coloured final product.

The solvent of ethanolic extracts can be replaced by a mixture of propanediol and water, to obtain an extract of *Mangifera indica* leaves provided in a mixture of propanediol and water as carrier solvent.

For example, one embodiment of the invention is the extract of *Mangifera indica* leaves extracted by a mixture of propanediol and water (extraction solvent) and provided in a mixture of propanediol and water as carrier solvent. In addition to other advantages described above, no solvent change step is required.

In a further aspect of the invention, the ratio of propanediol and water in the mixture used as as carrier solvent and/or extraction solvent is in the range between 1:1 and 5:1, preferably in the range between 2:1 and 4:1, more preferably 3:1.

For example, one embodiment of the invention is the extract of *Mangifera indica* leaves provided in a mixture of propanediol and water (3:1) as solvent.

The amount of plant material in the extract depends on extraction parameters like solvent, extraction time, temperature and others. Typically, the extract contains between 1-10% of plant material by weight, preferably between 1 to 5% of plant material by weight, more preferably between 1 to 3% of plant material by weight.

For example, one embodiment of the invention is the extract of *Mangifera indica* leaves comprising between 1 to 4.99% of plant material by weight, between 10 and 24.99% of water by weight, and more than 50% of propanediol by weight.

In a further aspect of the invention the extract of *Mangifera indica* leaves comprises at least one or more compounds selected from the group consisting of Mangiferin, Maclurin-glucoside, Gallotanin-glucoside and Iriflophenone-glucoside. In other words, the extract comprises one, two three or four compounds selected from the group consisting of Mangiferin, Maclurin-glucoside, Gallotanin-glucoside and Iriflophenone-glucoside.

In a further aspect of the invention the extract of *Mangifera indica* leaves comprises a mixture of Mangiferin, Maclurin-glucoside, Gallotanin-glucoside and Iriflophenone-glucoside.

Mangiferin (CAS No. 4773-96-0) is a glucoside of norathyriol; Maclurin-glucoside is more precisely Maclurin-3-C-β-glucoside (CAS No. 92631-83-9); Gallotanin-glucoside is more precisely penta-O-galloyl-β-D-glucoside (CAS No. 14937-32-7); and Iriflophenone-glucoside is more precisely Iriflophenone-3-C-glucoside (CAS No. 104669-02-5).

Mangiferin, Maclurin-glucoside, Gallotanin-glucoside and Iriflophenone-glucoside are phytomarkers, and fractions of a crude extract of *Mangifera indica* leaves comprising them were found to be particularly efficient on skin, for example efficient in sebum inhibition and in improving the quality of sebum. The mixture of those four phytomarkers is also referred to as pool of active molecules.

In a further aspect of the invention there is provided a method of preparing an extract of *Mangifera indica* leaves, comprising the steps of a) providing *Mangifera indica* leaves; and b) extracting *Mangifera indica* leaves.

Preferably, the *Mangifera indica* leaves are provided in smaller pieces prior to the extraction, in particular crushed, cut and/or ground. Optionally, the leaves may also be washed prior to the extraction.

By extracting, it is meant that the *Mangifera indica* leaves are treated with a solvent or a mixture of solvents. The extraction solvent can be selected from the group consisting of water, ethanol, propanediol and glycerol, or mixtures thereof, for example a mixture of ethanol and water, or a mixture of propanediol and water. The solvent(s) may also contain additives.

Suitable additives include, but are not limited to, acids, base, buffers, salts and/or co-solvents. In particular, the pH of the extraction solvent may be adjusted by the addition of acid (e.g. $H_2SO_4$ or citric acid) or base (e.g. NaOH).

In a further aspect of the invention, the extraction solvent is a mixture of propanediol and water. The ratio of propanediol and water is in the range between 1:1 and 5:1, preferably in the range between 2:1 and 4:1, more preferably 3:1.

It was found that the use of a mixture of propanediol and water in a ratio 3:1 as extraction solvent and carrier solvent was particularly advantageous.

The extraction may be performed at room temperature or at elevated temperature, e.g. at a temperature of about 40° C., about 60° C., or about 80° C. It was found that a temperature of about 60° C. was particularly advantageous.

A general extraction scheme is provided in FIG. 1. The leaves are provided in crushed form, and macerated with the extraction solvent. By removal of the solids during the solid-liquid separation, the crude extract is obtained.

Optionally, the crude extract may be purified, for example by filtration to obtain the final extract. Alternative purification methods are for example charcoal treatment and/or sterilizing filtration.

In a further aspect, the crude or final *Mangifera indica* leaves extract may be decolorated, for example by treatment with charcoal (powders or granulates), bentonite, or bleaching earths, for example tonsil 115 FF.

Optionally, the crude or final *Mangifera indica* leaves extract may also be concentrated.

Surprisingly, it was found that the *Mangifera indica* extract of the present invention possesses impressive skin care properties. In particular it is able to inhibit sebum production and to impact the quality of sebum. Furthermore, the *Mangifera indica* extract is able to reduce porphyrin on oily skin significantly. Also, the *Mangifera indica* extract can cause a progressive improvement of skin barrier. The reduction of sebum can also be observed on oily scalp and hair, when the *Mangifera indica* extract is used in hair care applications. The efficacy was demonstrated on multiple ethnicities.

So in a further aspect of the invention, there is provided the use of the *Mangifera indica* extract described above in skin care. Also, there is provided the use of the *Mangifera indica* extract described above in hair care.

In a further aspect, the present invention provides a cosmetic composition comprising a carrier and at least the *Mangifera indica* extract as an active ingredient. The carrier should be a dermatologically acceptable carrier.

In a particular embodiment, the cosmetic composition of the present invention is a skin care composition. In another particular embodiment, the cosmetic composition of the present invention is a hair care composition.

The cosmetic composition of the present invention shows impressive skin care, scalp and hair care properties, as demonstrated in different studies, explained in detail in the examples.

In an in vitro test it was demonstrated, that *Mangifera indica* extract is able to control the sebum production on human sebocyte cell line (see example 2). The test further permitted to identify the active molecules (also referred to as pool of active molecules) and to justify the role of the solvent.

In a further in vitro test it was demonstrated, that *Mangifera indica* extract is able to significantly reduce sebum production in different ethnicities (see example 3). In the literature, it has been described that the sebum production depends on gender and ethnicity (Shetage et al, 2018). Example 4 shows that *Mangifera indica* extract has a global impact on various pathways related to sebum production and lipogenesis regulation in each tested ethnicity.

In ex vivo tests it was demonstrated, that *Mangifera indica* extract does have a direct impact on human sebaceous glands. In particular, the extract is able to reduce the volume of the sebaceous glands (see example 5), reflecting the potential ability to accumulate sebum. On the other hand, it does not have any effect on sebaceous glands morphology or differentiation mechanism (see example 6). The analysis if *Mangifera indica* extract can affect the morphology of the glands was carried out using specific IHC (immunohistochemistry), using the immune detection of cytokeratin 7 (undifferentiated marker) and adipophilin (differentiated marker), two markers of sebocytes differentiation. *Mangifera indica* extract acts as a sebo-regulator but does not influence sebocyte differentiation.

It was further evaluated, whether *Mangifera indica* extract has an impact on the quality of sebum (example 7). It was found, that *Mangifera indica* extract can cause an improvement of sebum quality as observed by the reduction of triglyceride and squalene contents which are increased by lipogenic stimulation. Interestingly, these two lipid families are found to be significantly increased in the sebum coming from people with acne conditions (Pappas, 2009 and Picardo et al, 2009). It can be followed that by reducing the quantity of sebum and by improving its quality, the skin condition can be restored to normal one.

By an in tubo assay, it was demonstrated that *Mangifera indica* extract is able to inhibit the growth of several bacteria which can be found on oily skin (example 8).

In clinical tests, a reduction of sebum content (example 9d), a reduction of porphyrin intensity (example 90 and an improvement of skin barrier (example 9h) was observed on Caucasian volunteers. Furthermore, an improvement of sebum quality was observed, in particular an improvement of TG/FFA ratio (example 9j) and an improvement of SQOOH/SQ ratio (example 9k). These results demonstrate an improvement of sebum quality suggesting an impact on skin microbiota.

An analysis of skin microbiota (example 10) evidenced, that a placebo can induce a dysbiosis, while the addition of *Mangifera indica* extract protects the skin microbiota composition, while reducing the sebum quantity.

Overall, *Mangifera indica* extract is microbiome friendly and promotes micro rebalancing effect on skin microbiota targeted the *acnes* phylotype of *P. acnes* without changing the global microbial composition.

Furthermore, a reduction of sebum content was observed on Asian and African volunteers (examples 11 and 12).

In example 13, the reduction of sebum on oily scalp and hair was shown.

In silico analysis (example 14) showed that Mangiferin is able to bind to PPAR-γ with a very low binding energy. Indeed, no unfavourable residues to the interaction between the both elements have been identified. A molecular dynamic study evidenced that the complex is very stable during the simulation time predicting that the Mangiferin can interact with PPAR-γ.

Another in silico study (example 15) showed what kind of biological efficacy Maclurin and Iriflophenone can have. The results demonstrated that both molecules seems to be involved in sebo-regulation as observed by their strong homology and potential interaction with proteins involved in lipogenesis lined to sebum production. Overall, *Mangifera indica* extract has a strong sebo-regulation activity by the control of lipid synthesis from sebaceous glands. In vitro and ex vivo biological models using sebocytes and sebaceous gland or skin explant containing them were used in order to prove its biological efficacy.

Thus, in conclusion, the composition of the present invention provides a reduction of sebum production, a reduction of the volume of the sebaceous glands, an improvement of sebum quality, an improvement of acne conditions, a reduction of porphyrin intensity, an improvement of skin barrier, in particular prevention of dry skin. The composition also has an antibacterial effect. The composition is microbiome friendly and has a micro rebalancing effect on acneic phylotype of *P. acnes* (IA1).

Therefore, the composition of the present invention may be used in skin care applications for oily and greasy skin and anti-acne applications.

The skin care applications can be selected from the group consisting of serums, anti-aging day and night creams, lotions, essences, masks and others.

Also, the composition of the present invention may be used in scalp and hair care applications for oily and greasy scalp and hair.

The scalp and hair care applications can be selected from the group consisting of shampoos, conditioners, powders, creams and others.

In a further aspect, the present invention relates to a method of regulating the sebum production by applying the cosmetic composition described above to human skin or scalp and hair.

The present invention is further illustrated by means of the following non-limiting examples:

EXAMPLES

General: *Mangifera indica* leaves have been obtained from Sama Bioconsult, Burkina Faso. Alternatively, leaves can be obtained from International Trade Development (ITRAD), Ivory coast. The leaves have been collected and dried. Dried leaves were grounded to a particle size of 1.5 mm.

Example 1 a) Preparation of an Extract of *Mangifera indica* Leaves 80 g of crushed dried leaves of *Mangifera indica* have been macerated with 1000 g of propanediol/water in a ratio of 3:1 by weight during 4 hours at 60° C. The plant parts have been removed by centrifugation during 15 minutes at 4000 rpm. The remaining solution has been filtered on filter Filtrox reference AF31H (12-5 μm) followed by a sterilized filtration on filter Filtrox reference AF ST145 (0.3-0.1 μm). The final extract has been stored at room temperature protected from light.

b) Fractionation and Analysis of the Extract

The extract has been fractionated by CPC (Centrifugal Partition Chromatography)

- Injected mass: 2.5 g of dry extract
- CPC instrument FCPE300® (Rousselet Robatel Kromaton)—column of 303 mL
- Two-phase solvent system: MtBE/ACN/$H_2O$ (3:3:4, v/v)→total volume 4 L
- Stationary phase: lower phase of the solvent system
- Mobile phase: upper phase of the solvent system
- Column rotation speed: 1200 rpm
- Flow rate: 20 mL/min An isocratic elution of the first mobile phase was performed in the ascending mode for 87 minutes. Then the column was extruded for 15 minutes. The CPC chromatogram was monitored at 205, 254 and 366 nm. Fractions of 20 mL were collected over the whole experiment and combined according to their thin layer chromatography profiles. As a result, 15 sub-fractions were obtained.

An aliquot of each fraction from F1 to F15 (up to ~20 mg) was dissolved in 600 μL DMSO-d6 and analyzed by $^{13}$C NMR at 298 K on a Bruker Avance AVIII-600 spectrometer (Karlsruhe, Germany) equipped with a TXI cryoprobe. Spectra were manually phased, baseline corrected using the TOPSPIN 3.2 software (Bruker), and calibrated on the central resonance of DMSO-d6 (δ 39.80 ppm). The absolute intensities of all $^{13}$C NMR signals were automatically collected and binned across the spectra of the fraction series by using a locally developed computer script. The resulting table was imported into the PermutMatrix version 1.9.3 software (LIRMM, Montpellier, France) for Hierarchical Clustering Analysis. The resulting 13C chemical shift clusters were visualized as dendrograms on a two-dimensional map: the higher the intensity of $^{13}$C NMR signals, the brighter the color on the map.

In parallel, a literature survey was performed to obtain names and structures of a maximum of metabolites already described in the genus *Mangifera* (n=51). For metabolite identification, each 13C chemical shift cluster obtained from HCA was manually submitted to the structure search engine of the database management software.

Additional 2D NMR experiments (HSQC, HMBC, and COSY) were performed on fractions containing putatively identified compounds in order to confirm the molecular structures proposed by the database at the end of the dereplication process.

In addition, LC-MS (liquid chromatography coupled to mass spectrometry) was used, and 13 compounds have been characterized based on internal database and comparison of literature data. HPLC (High Performance Liquid Chromatography) was used to further analyse the extract with UV detection at 315 nm and 295 nm, in particular the amount of the four main phytomarkers, which have been quantified in different batches as follows:

TABLE 1

| Batch | Use of extract | Mangiferin content (in ppm) | Iriflophenone-C-glucoside content (in ppm) | Maclurin-C-glucoside content (in ppm) | penta-O-galloyl-glucoside (in ppm) |
|---|---|---|---|---|---|
| a | In-vitro and ex-vivo tests | 1961.0 | 65.6.0 | 834.5 | 958.0 |
| b | clinical studies | 1896.0 | 434.3 | 278.2 | 816.0 |
| c | clinical studies | 1679.8 | 366.8 | 245.1 | 839.0 |

Example 2. In Vitro Lipogenesis Inhibition in Human Sebocytes Cell Line a) Cell Culture and Treatment The sebocytes were seeded in 96-well plates (50 000 cells/well) and cultured for 24 hours in culture medium. The medium was then removed and replaced by assay medium containing the tested products including *Mangifera indica* extract at 0.3%, Mangiferin alone or pooled active molecules (four main phytomarkers) at their equivalent dosage in the extract at 0.3%. In the control assay medium, no product was contained. The cells were preincubated for 4 hours at those conditions. Then, the lipogenic mix (containing vitamin C, vitamin D3, insulin and calcium, and no androgens) was added in order to mimic the condition of excess of sebum, and the cells were incubated for 7 days. At mid-term, i.e. after 3 days of incubation, half of the medium was removed and the treatments were renewed (including lipogenic mix stimulation). A non-stimulated control condition was performed in parallel. All experimental conditions were performed in n=3, except for stimulated control conditions in n=6.

b) Analysis of the Lipid Content (Bodipy® Labeling)

At the end of the incubation, the cells were rinsed, fixed and permeabilized. The lipid droplets contained in the cells were then labeled using a specific Bodipy® fluorescent lipid probe labeling mainly neutral lipids. In parallel, the cell nuclei were stained using a Hoechst 33258 (bis-benzimide) solution. The acquisition of the images was performed using INCell Analyzer™ 1000 (GE Healthcare). Ten photos were taken per well for each labeling (×20 objective lens). The labeling was quantified by the measurement of the fluorescence intensity normalized to the total number of cells (Integration of numerical data with the Developer Toolbox 1.5, GE Healthcare software). Results were expressed as Fluorescence intensity normalized to the number of cells, % stimulated control and % inhibition. The fluorescence intensity was analyzed exclusively in the lipid droplets (image analysis program based on object segmentation). Therefore non-specific fluorescent background signal, which can be frequently observed in high confluence cultures of SEBO662AR, was not taken into account in the image analysis.

c) Identification of Seboregulation Activity

Figure 2:
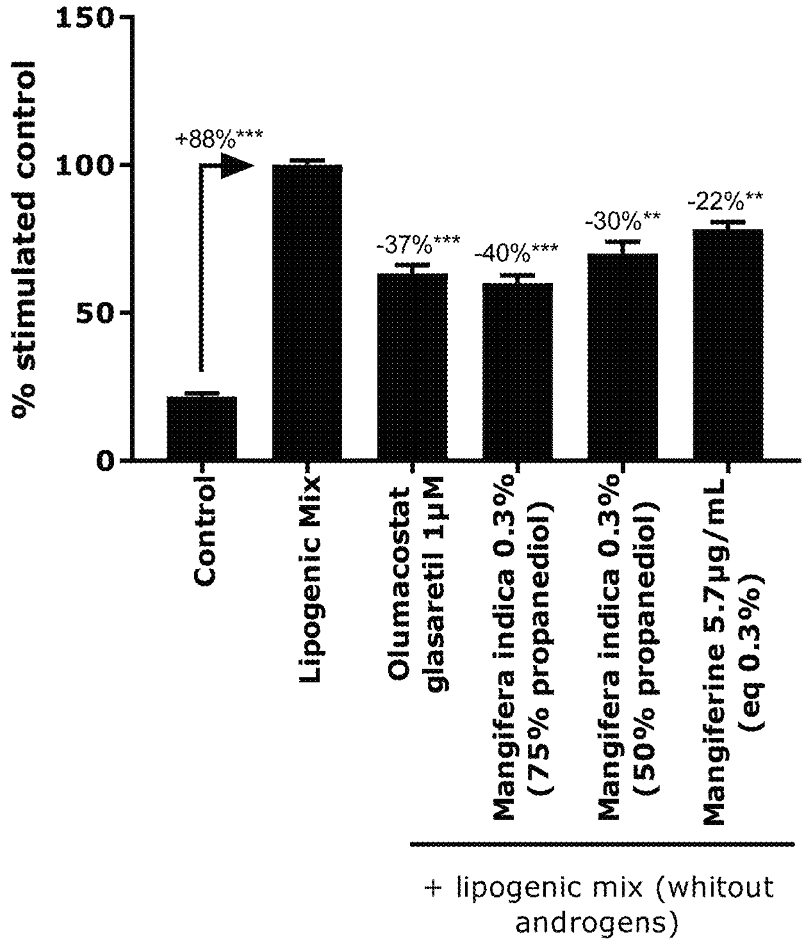
FIG. 2 shows a lipid accumulation analysis measured by quantification of fluorescence intensity Bodipy®.

FIG. 2 shows a lipid accumulation analysis measured by quantification of fluorescence intensity Bodipy®. The results are expressed in percent of Mix lipogenic condition (% stimulated control). Student T test was used to determine the significance of the data with * $p<0.01$ and ** $p<0.001$.

A significant increase of lipid detection after 7 days of lipogenic mix exposure was observed. It is significant reduced by Olumacostat glasaretyl at 1 μm (positive control). Indeed Olumacostat glasaretil showed a significant reduction of lipid production by −37% compared with lipogenic mix condition after 7 days. A similar activity has been observed after 7 days of treatment with two *Mangifera indica* extracts at 0.3%; the extract at 50% propanediol and 75% propanediol evidenced a reduction by −30% and −40%, respectively.

Mangiferin (the major compound of the extract) was tested alone in order to evaluate its ability to decrease the lipogenesis. Mangiferin was used at the same amount as available in the extracts. Mangiferin was able to reduce the lipogenesis by −22% compared with lipogenic mix condition.

Figure 3:
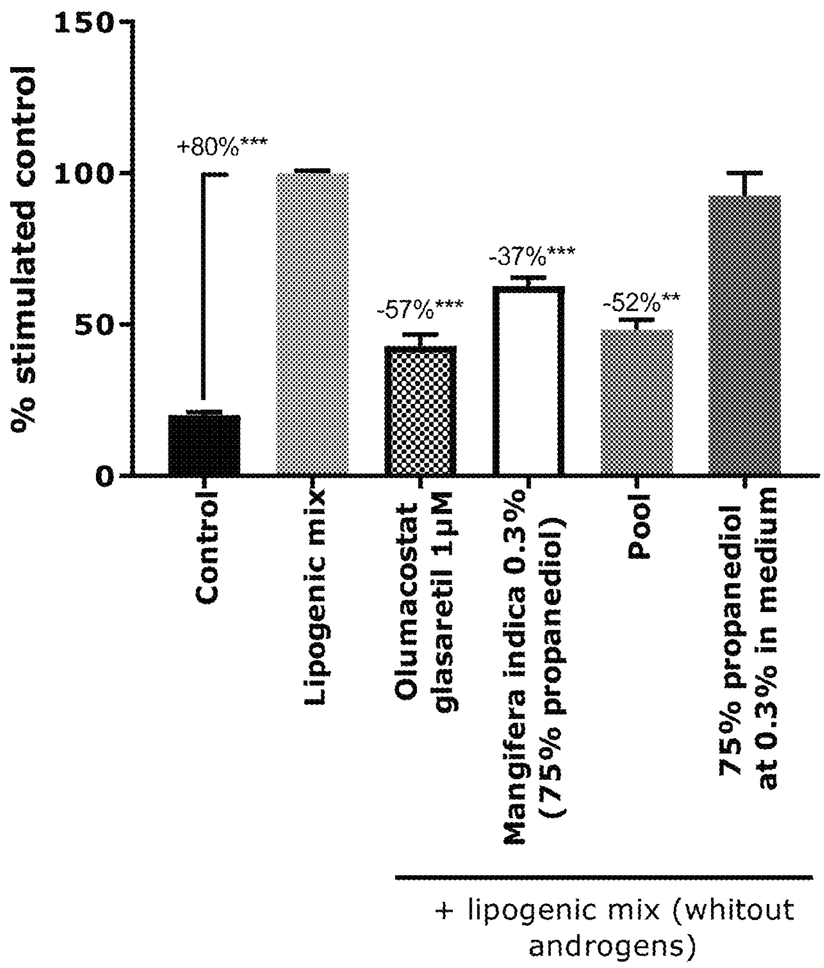
FIG. 3 shows a lipid accumulation analysis measured by quantification of fluorescence intensity Bodipy®.

This first result demonstrated that *Mangifera indica* extract is able to control the sebum production from sebocyte cell line. It further shows that the Mangiferin is able to inhibit the sebum production; however it seems not to be the only compound responsible for the biological activity of *Mangifera indica* extract. There are probably other actives molecules involved in this seboregulation activation.

d) Impact of the Pool of Active Molecules from *Mangifera indica* Extract on Sebum Inhibition FIG. 3 shows a lipid accumulation analysis measured by quantification of fluorescence intensity Bodipy®. The results are expressed in percent of Mix lipogenic condition (% stimulated control). Student T test was used to determine the significance of the data with  $p<0.01$ and * $p<0.001$.

As demonstrated, also other compounds of the *Mangifera indica* extract are involved in the inhibition of sebum production. Using the same model based on the induction of sebum production in vitro by a lipogenic mix on sebocytes cell line it was demonstrated that the pool of molecules (Mangiferin, Maclurin, Gallotanin and Iriflophenone) at equivalent dosage found in the extract at 0.3% was very efficient on the inhibition of sebum production showing −52% in comparison with lipogenic mix condition. This effect was even higher than *Mangifera indica* extract in propanediol 75% at 0.3% which demonstrated that the pool of molecules was entirely responsible for the seboregulation activity of the full extract.

It was further shown that the propanediol 75% alone at 0.3% did not induced any significant effect on sebum production inhibition under the same experimental conditions. This result proves that the efficacy of the extract is only related to *Mangifera indica* extract and not promoted by propanediol.

Example 3. In Vitro Lipogenesis Inhibition in Human Sebocytes Cell Line Derived from iPS with Three Ethnicities a) Cell Culture and Treatment In order to demonstrate the efficacy of *Mangifera indica* extract on the most representative ethnicities of the world, it was decided to work on real sebocytes derived from iPS. Thank to this technique, various donors representing Caucasian, Asian and African ethnicities could be selected. The study was performed in presence of arachidonic acid 5 (AA5), which is an inductor of lipogenesis and differentiation of the sebocytes, in order to mimic the condition of excess of sebum.

hiPSC derived sebocytes (Phenocell) were cultured in a 37° C., 5% $CO_2$ incubator, on fibronectine coated plates for 3 days in complete PhenoCULT-SEB medium (Phenocell). Lipid production was subsequently induced using 5 μM arachidonic acid (Sigma, cat. 10931) treatment for 96 hours in basal PhenoCULT-SEB (Phenocell), while 10 μM 13-cis-retinoic-acid (Tocris, cat.5513) was used as a reference inhibitor. The active was tested at 0.3% in the medium in presence of arachidonic acid.

b) Analysis of the Lipid Content (Bodipy® Labeling)

Figure 4:
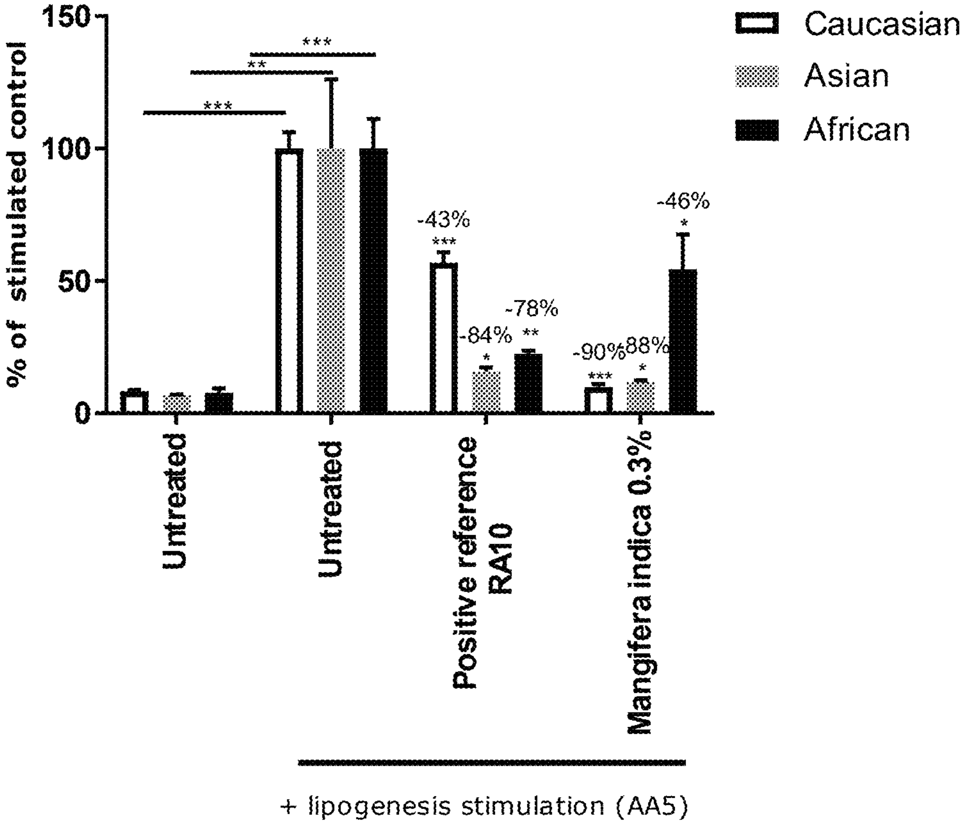
FIG. 4 shows a lipid accumulation analysis measured by quantification of fluorescence intensity.

Following treatment, cells were fixed and stained with BODIPY 493/503 (Thermofisher, cat.D3922). Stained cell pictures were acquired and analyzed with an automated imager (CX5 Cellinsight, Thermofisher). An average of 40 microscope fields was taken for each well.

c) In Vitro Lipogenesis Inhibition in Sebocytes Derived from iPS (Induced Pluripotent Stem) Cells with Three Ethnicities FIG. 4 shows a lipid accumulation analysis measured by quantification of fluorescence intensity. The results are expressed in percent of stimulated control. ANOVA multi comparison was used to determine the significance of the data with * p<0.05,  p<0.01 and * p<0.001.

A significant reduction of lipids production in each ethnicity has been observed after application of reference inhibitor 13-cis-retinoic-acid at 10 μM (RA10). These results validated the experimentation and used model.

The application of *Mangifera indica* extract at 0.3% showed slight variation on the reduction of sebum production in different ethnicities. Indeed, *Mangifera indica* extract was very efficient on Caucasian sebocytes as observed by the reduction of lipid detection by −90%. Similar efficiency was demonstrated on Asian sebocytes showing a reduction of sebum production by −88%. Also a reduction of sebum production by −46% was observed on African sebocytes, but this efficiency it slightly lower than for the other ethnicities. Overall, these results demonstrated that *Mangifera indica* extract at 0.3% was able to significantly reduced sebum production on all ethnicities.

Example 4. Identification of the Mode of Action by qPCR a) Method

In order understand the potential mode of action of *Mangifera indica* extract there was conducted a transcriptomic analysis on the three previous ethnicities. Various genes coding for transcription factors and enzymes involved in sebum production in the skin have been specifically analysed. The biological markers have been chosen according to their involvement in the sebum production in the skin:

- FDFT1 (squalene synthase) to represent the synthesis of squalene.
- PPARG (Peroxisome proliferator-activated receptor gamma), a transcription factor involved in the global lipogenesis.
- DGAT2 (diacylglycerol acyltransferase) to represent the synthesis of triglycerides.
- FADS2 (Fatty acid desaturase-2) which catalyse a reaction specific to a sebum compound.

RNA from sebocytes derived from iPS were extracted using Isolate II RNA mini kit (Bioline, cat.BIO-52073), according to the manufacturer's instructions. Reverse-transcription was performed using SensiFast Synthesis kit (Bioline, cat.BIO-65054) on 250 ng total RNA per sample. Finally, real-time quantitative PCR was done using Itaq universal SYBR Green Supermix (Biorad, cat.1725125) in a CFX96 thermocycler (Biorad). The PT-SEB-RNA primer panel (Phenocell) including PPARG (Peroxisome proliferator-activated receptor gamma), DGAT2 (diacylglycerol acyltransferase), FADS2 (Fatty acid desaturase-2) and FDFT1 (squalene synthase) was used for this assay.

b) Results

Figure 5A:
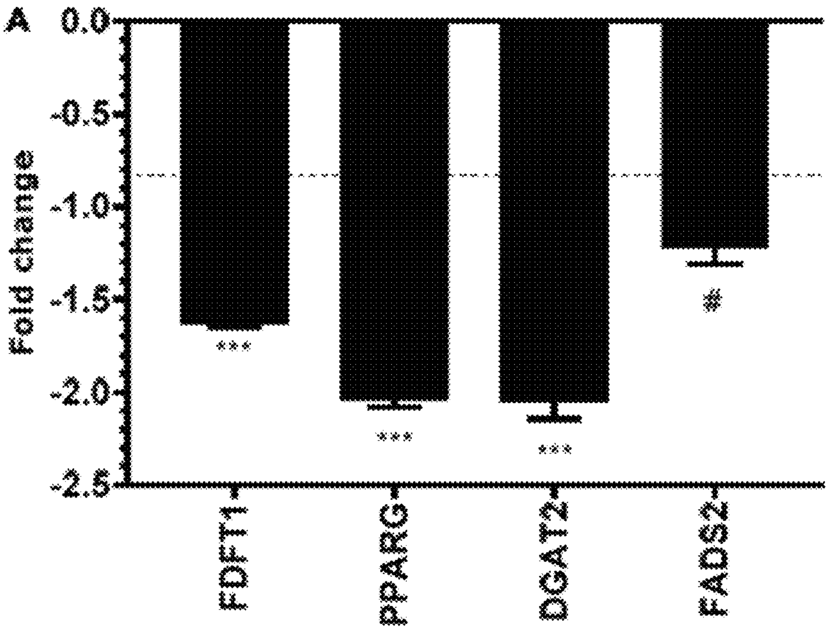
FIG. 5*a* shows relative gene expressions of the condition treated with *Mangifera indica* extract at 0.3% compared to the untreated condition and shows mean of fold change for the three ethnicities.
Figure 5B:
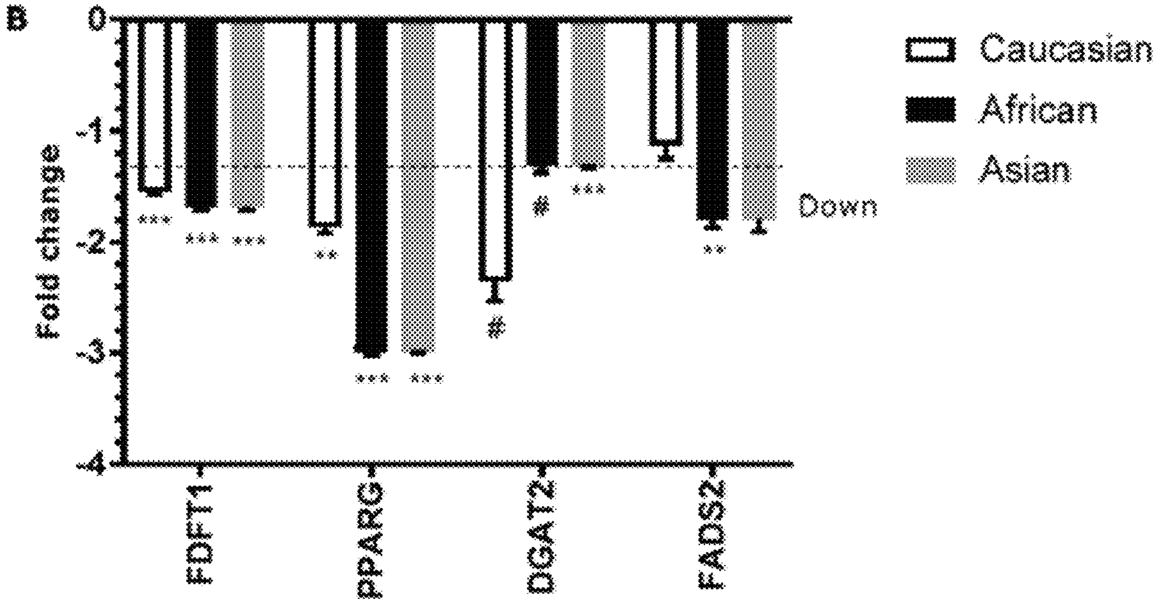
FIG. 5*b* shows relative gene expressions of the condition treated with *Mangifera indica* extract at 0.3% compared to the untreated condition and shows fold change for each ethnicity.

FIG. 5 shows relative gene expressions of the condition treated with *Mangifera indica* extract at 0.3% compared to the untreated condition. FIG. 5*a* shows mean of fold change for the three ethnicities, FIG. 5*b* shows fold change for each ethnicity. A fold change is the induction of gene expression between the untreated and stimulated condition for each gene. ANOVA multi comparison was used to determine the significance of the data with #p<0.1,  p<0.01 and * p<0.001

FIG. 5*a* shows that all the gene's expressions were decreased in presence of *Mangifera indica* extract at 0.3%. More precisely, a significant down-regulation of the genes coding for FDFT1, PPARG, DGAT2 and FADS2 showing the fold change f −1.6, −2.0, −2.0 and −1.2 has been observed.

The impact on the different ethnicities is shown in FIG. 5*b*. It was observed that *Mangifera indica* extract significantly down-regulated FDFT1 and PPARG expressions on each ethnicity. The down regulation of DGAT2 expression was only significant in Asian donor, while the down-regulation of FADS2 expression was significant in African donor. These results confirmed that *Mangifera indica* extract had a global impact on various pathways related to sebum production and lipogenesis regulation in each ethnicity.

Example 5. Ex Vivo Sebaceous Gland Volume Reduction Analysis a) Cell Culture and Treatment The test was carried out on 4 skin explants NativeSkin® (average 40.75 years old) from pelvic area, a full-thickness skin biopsy embedded in a solid and nourishing matrix while its epidermal surface is left in contact with air. The skin biopsy is firmly embedded in the matrix that prevents any lateral diffusion of topically applied formulations.

The skin explants were treated topically once a day for 7 days in presence of linoleic acid at 10% in Carbopol Ultrez 10 in order to stimulate the lipogenesis and mimic the condition of sebum excess (stimulated condition) or treated with Carbopol only (control condition).

This induction mimics a high production of sebum. In parallel, skin explants were treated in presence of *Mangifera indica* extract at 1% and 2% formulated in Carbopol. After treatment, skin explants were fixed in formalin.

b) Study of Sebaceous Glands Volume in 3D

After fixation, skin explants were cleared with methanol and a mix of Benzyl Benzoate and Benzyl Alcohol. All samples were observed by fluorescence light sheet microscopy (SPIM, homemade fabrication). Stack of images were taken per sample. 3D pictures of the glands were reconstructed and the size of each sebaceous gland was quantified using Amira® software. Results were represented with the mean volume of sebaceous gland+/−standard error to the mean.

c) Results

Figure 6:
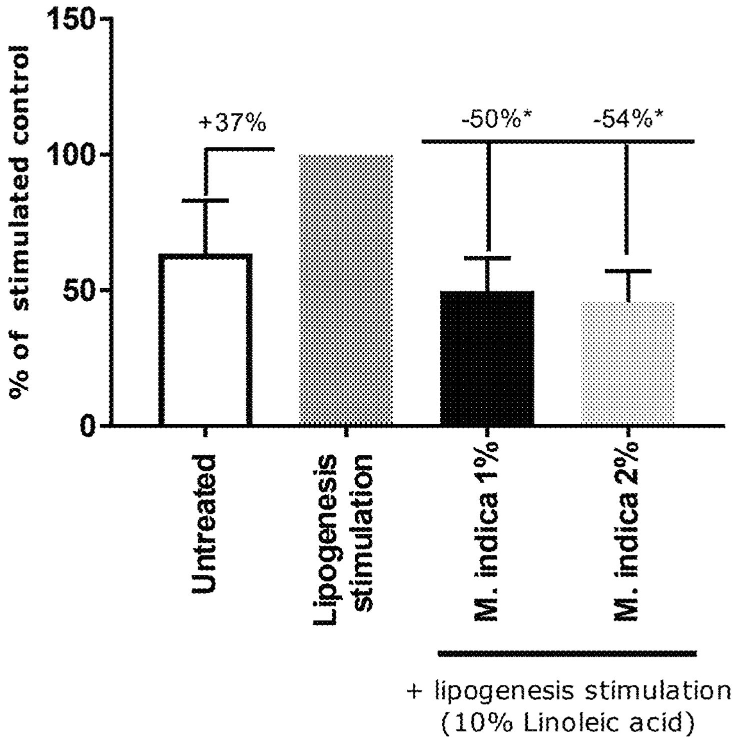
FIG. 6 shows the 3D volume of sebaceous glands.

FIG. 6 shows the 3D volume of sebaceous glands. The results are expressed in percent of the stimulated control (10% linoleic acid). Mann Whitney test was used to determine the significance of the data with * p<0.05.

Linoleic acid stimulation for 7 days increased the 3D volume of sebaceous glands by +37%. The *Mangifera indica* extract reduced the 3D volume of the sebaceous glands significantly by −50% (p<0.05) at 1% and by −54% (p<0.05) at 2% of the extract formulated in Carbopol.

Example 6. Ex Vivo Integrity of Sebaceous Glands a) Cell Culture and Treatment See example 5, section a b) Study of Differentiation and Structure of Sebaceous Glands After fixation, skin explants were included in paraffin and sectioned. Skin sections were stained by an immunostaining technique to detect specifically Adipophilin (ADFP) and Cytokeratin 7 (CK7), which are two markers of sebocytes differentiation. The staining was observed using fluorescent microscopy (LEICA DM5000). Around 10 images were taken per sample. Relative fluorescence of protein was quantified for all images. Results were represented with the mean fluorescence intensity of protein+/−standard error to the mean.

c) Results

FIG. 7 shows the quantification of fluorescence of Cytokeratin 7 and adipophilin. The results are expressed in percent of the stimulated control (10% linoleic acid). Mann Whitney test was used to determine the significance of the data with non-significant results $p>0.05$.

Figure 7B:
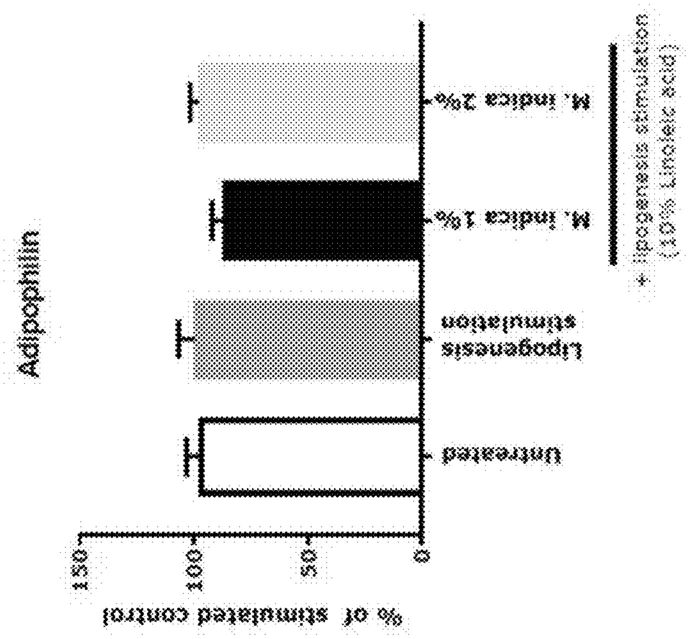
FIG. 7*b* shows the quantification of fluorescence of adipophilin.
Figure 7A:
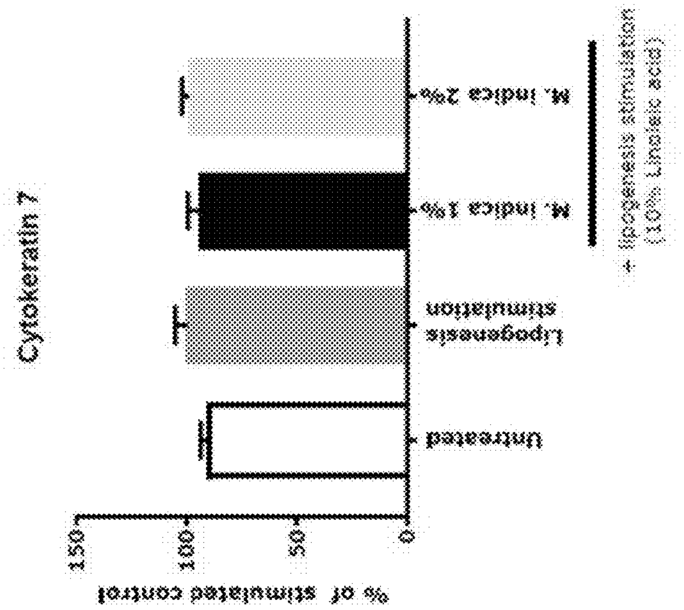
FIG. 7*a* shows the quantification of fluorescence of Cytokeratin 7.

It was shown that after the treatment with *Mangifera indica* extract, there was no impact on the expression of these two markers as observed by the level of fluorescence intensity (FIGS. 7*a* and 7*b*). After quantification of the fluorescence signal, it was also shown that there was no significant difference caused by treatment with *Mangifera indica* extract in comparison to untreated conditions. It can be concluded that *Mangifera indica* extract does not have any effect on sebaceous glands morphology or differentiation mechanism.

Example 7. Ex Vivo Sebum Quantification a) Cell Culture and Treatment

Skin explants from lifting of 3 donors (average 56.7 years old) were treated in systemic every day during 5 days in presence of dihydrotestosterone (DHT) at 30 μM to induce an increase of lipogenesis mimicking a high production of sebum condition (stimulated condition) or left untreated (control condition). In parallel, skin explants were treated in presence of 0.5% of dibenzoyle peroxide (POB, positive reference) or with the *Mangifera indica* extract at 1% and 2%.

b) Lipids Extraction

The tissues are extracted with an aqueous cocktail overnight at 4° C. They are then treated to take off the epidermis. A specific technique is used to recover the glands attached to these hair shafts.

After rinsing in an isotonic medium, the epidermis and its appendages are transferred to a watch glass. The sebaceous glands attached to the hair shaft of hair follicles are cut at the level of the pilosebaceous canal and deposited against the walls of the recovery vials. The sebaceous glands are recovered after dilaceration of the epidermal fragments. The glands are collected in a batch of 10 units. A washing of the glands is then performed to eliminate any contaminations of non-sebaceous origin. The sebum is then extracted with an organic cocktail overnight at room temperature. From this lipid extract, purification was carried out in order to isolate the different classes of lipids.

c) Lipids Analysis and Quantification

The identification and quantification of the different classes of lipids was realized by GC/MS.

d) Results—Analysis and Quantification of Sebum

FIG. 8 shows Lipids extraction from sebaceous glands and quantification measured by GC/MS or LC/MS. The results are expressed in percent of the stimulated control (Untreated+DHT 30 μM). Bonferroni test multi comparison was used to do statistical analysis with #$p<0.1$, * $p<0.05$, $p<0.01$, * $p<0.001$.

The sebum produced on human sebaceous glands was extracted, and four families of lipids were identified, which are squalene, cholesterol, free fatty acids and triglycerides.

Figure 8A:
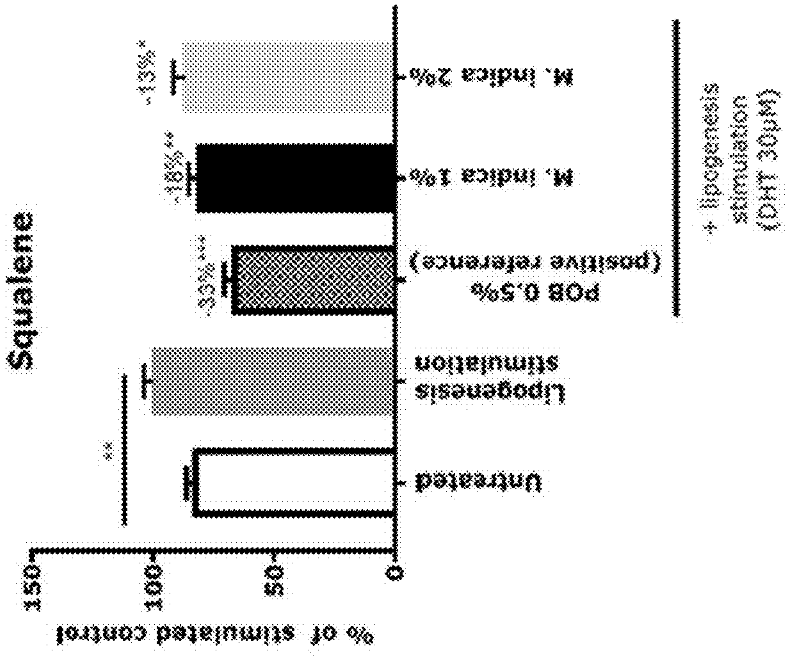
FIG. 8*a* shows Lipids extraction from sebaceous glands and quantification measured by GC/MS or LC/MS and shows that stimulation by dihydrotestosterone (DHT) induced a significant increase of squalene.
Figure 8B:
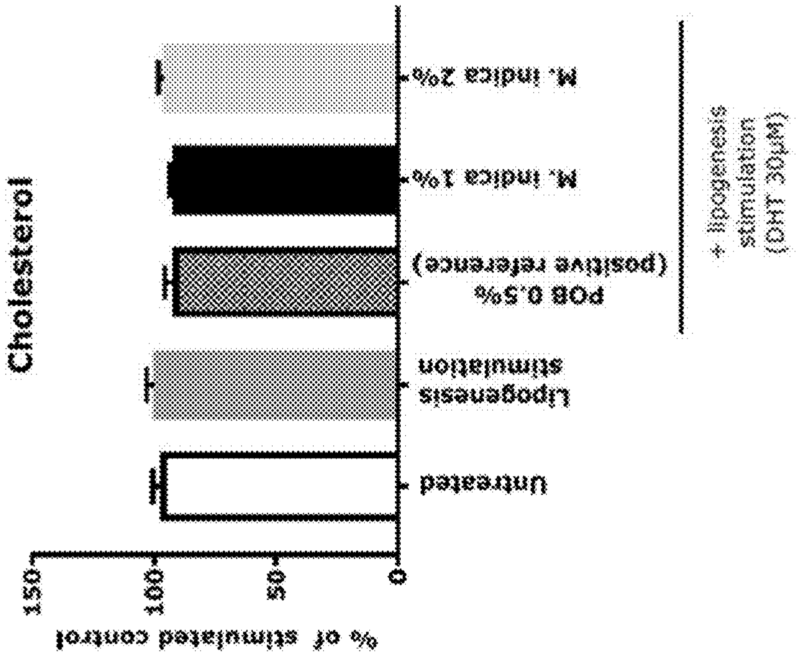
FIG. 8*b* shows Lipids extraction from sebaceous glands and quantification measured by GC/MS or LC/MS and shows that there was no effect on cholesterol with the stimulation by dihydrotestosterone (DHT).
Figure 8C:
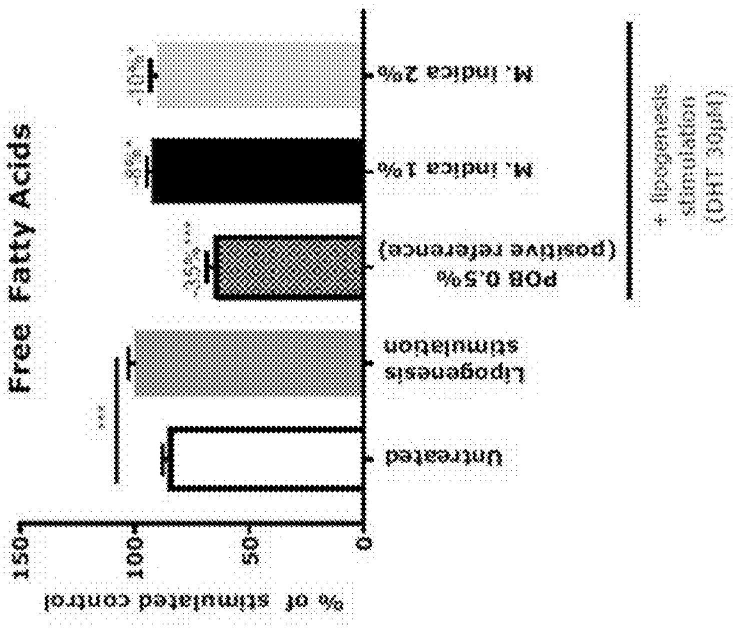
FIG. 8*c* shows Lipids extraction from sebaceous glands and quantification measured by GC/MS or LC/MS and shows that stimulation by dihydrotestosterone (DHT) induced a significant increase of free fatty Acids.

This stimulation by dihydrotestosterone (DHT) induced a significant increase of squalene, free fatty Acids (FFAs) and triglycerides (FIGS. 8*a*, *c*, and *d*). There was no effect on cholesterol family (FIG. 8*b*). The positive reference (POB at 0.5%) showed a significant reduction in each family excepted for the cholesterol validating the experiment.

Figure 8D:
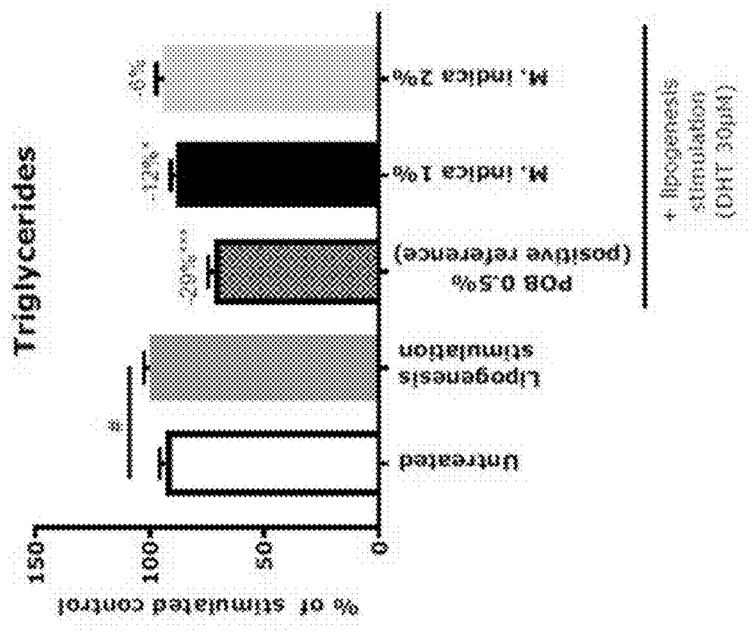
FIG. 8*d* shows Lipids extraction from sebaceous glands and quantification measured by GC/MS or LC/MS and shows that stimulation by dihydrotestosterone (DHT) induced a significant increase of triglycerides.

*Mangifera indica* extract at 1% and 2% shows an improvement of sebum quality as observed by the reduction of triglyceride and squalene contents which are increased by lipogenic stimulation (FIGS. 8*d* and *a*).

Example 8. In Tubo Evaluation—Determination of Potential Bacterial Inhibitor Activity on Bacteria Present in Oily Skin The potential bacterial inhibitor activity of *Mangifera indica* extract on *Propionibacterium acnes* (*P acnes*, also known as *Cutibacterium acnes* (*C. acnes*)), *Cutibacterium granulosum* (*C. granulosum*), *Staphylococcus aureus* (*S. aureus*), and *Haemophilus influenza* (*H. influenza*) has been assessed. Those bacteria can be found on oily skin.

a) MIC (Minimum Inhibitory Concentration) Evaluation

The minimum inhibitory concentration of the following active ingredients has been assessed:

- *Mangifera indica* extract (in propanediol/water 75/25);
- Vehicule (propanediol/water 75/25, expressed as Activolo3-75%);
- "Pool Mangiferin" which is the pure molecule mangiferin at the same concentration in the *Mangifera indica* extract in propanediol/water 75/25
- "Pool *Mangifera*" with is the mix of the 4 molecules (mangiferin, maclurin-C-glucoside, irifluophenone-C-glucoside, gallotanin) at the same concentration in the *Mangifera indica* extract in propane-diol/water 75/25.

Acneic phylotype IA1 *P. acnes* (American Type Culture Collection ATCC 6919) and *C. granulosum* (ATCC 25564) were cultured in reinforced clostridial broth (RCB) as recommended by ATCC. pH was adjusted at 6.8+/−0.2 (25° C.) (launch of culture at D−2).

After two days, the bacterial concentration was adjusted in reinforced clostridial broth to obtain a solution at $1 \cdot 10^6$ CFU/ml ($5 \cdot 10^4$ CFU/well). The potential inhibitors have been added at different concentrations in water (MIC evaluation at D0). Two days later, the inhibition of *P. acnes* and *C. granulosum* was evaluated using Colony counter IUL instruments, flash and go model (reading at D2).

*S. aureus*: The day before the experiment *S. aureus* (ATCC 33592) was plated and grown overnight at 37° C. Colonies were resuspended in 5 mL of TSB (Tryptic Soy Broth) to obtain a 0.5 McFarland D0 (~$1 \cdot 10^8$ CFU/ml) (launch of culture at D−1). The potential inhibitor has been added at different concentrations in water (MIC evaluation at D0). One day later, the inhibition of *S. aureus* was evaluated using Colony counter IUL instruments, flash and go model (reading at D1).

*H. influenzae* (ATCC 49766) was cultured in Mueller Hinton broth as recommended by ATCC with 5% $CO_2$. The Bacterial concentration was adjusted in Mueller Hinton broth to obtain a solution at $1 \cdot 10^6$ CFU/ml ($5 \cdot 10^4$ CFU/well) (launch of culture at D−2). The potential inhibitor has been added at different concentrations in water (MIC evaluation at D0). Two day later, the inhibition of *H. influenzae* was evaluated using Colony counter IUL instruments, flash and go model (reading at D2).

The design plate is presented in Table 2 below. Concentrations are expressed in % (m/v).

TABLE 2

| | 1 | 2 | 3 | 4 | 5 | 6 | 7 | 8 | 9 | 10 | 11 | 12 |
|---|---|---|---|---|---|---|---|---|---|---|---|---|
| A | neg. control | pos. control | pure | Dilution ½ | Dilution ¼ | Dilution ⅛ | Dilution 1/16 | Dilution 1/32 | Dilution 1/64 | Dilution 1/128 | Dilution 1/256 | Dilution 1/512 |
| B | | | pure | pure | pure | pure | pure | 16 $10^{-4}$ | 16 $10^{-4}$ | 16 $10^{-4}$ | 16 $10^{-4}$ | 16 $10^{-4}$ |
| C | | | 2% | 1% | 0.5% | 25.0 $10^{-2}$ | 12.5 $10^{-2}$ | 6.25 $10^{-2}$ | 3.13$10^{-2}$ | 1.56 $10^{-2}$ | 0.78 $10^{-2}$ | 0.39 $10^{-2}$ |
| D | | | 2% | 1% | 0.5% | 25.0 $10^{-2}$ | 12.5 $10^{-2}$ | 6.25 $10^{-2}$ | 3.13$10^{-2}$ | 1.56 $10^{-2}$ | 0.78 $10^{-2}$ | 0.39 $10^{-2}$ |
| E | | | 2% | 1% | 0.5% | 25.0 $10^{-2}$ | 12.5 $10^{-2}$ | 6.25 $10^{-2}$ | 3.13$10^{-2}$ | 1.56 $10^{-2}$ | 0.78 $10^{-2}$ | 0.39 $10^{-2}$ |
| F | | | 2% | 1% | 0.5% | 25.0 $10^{-2}$ | 12.5 $10^{-2}$ | 6.25 $10^{-2}$ | 3.13$10^{-2}$ | 1.56 $10^{-2}$ | 0.78 $10^{-2}$ | 0.39 $10^{-2}$ |
| G | | | 2% | 1% | 0.5% | 25.0 $10^{-2}$ | 12.5 $10^{-2}$ | 6.25 $10^{-2}$ | 3.13$10^{-2}$ | 1.56 $10^{-2}$ | 0.78 $10^{-2}$ | 0.39 $10^{-2}$ |
| H | | | 2% | 1% | 0.5% | 25.0 $10^{-2}$ | 12.5 $10^{-2}$ | 6.25 $10^{-2}$ | 3.13$10^{-2}$ | 1.56 $10^{-2}$ | 0.78 $10^{-2}$ | 0.39 $10^{-2}$ |

A: Activolo3-75%*; B: Activolo3-75% (Col. 3-7) and Ciprofloxacin (Col. 8-12); C and D: *Mangifera indica* extract*; E and F: pool mangiferin*; G and H: pool mangifera*; Dilution of actives marked with a star have been performed with water. This meaning does also apply to the following Tables 3 to 6.

The diluted bacterial suspension was added to columns 2 to 12. RCB medium was added to column 1 as negative control.

Optical density was determined, which correlates to the bacterial growth. Thereafter, an inhibition value (%) was determined for each condition using the following formula:

$$\text{Inhibition value (\%)} = 100 - \frac{(\text{Condition } i - \text{Negative control})}{(\text{Positive control} - \text{Negative control})} * 100$$

The percentage of inhibition must be higher or equal than 90% to reach the MIC.

Results:

*C. acnes*, Bacterial suspension concentration: $1.46 \cdot 10^{6}$ CFU/ml

TABLE 3a

| Optical density, *C. acnes*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0.048 | 0.217 | 0.052 | 0.050 | 0.049 | 0.131 | 0.226 | 0.225 | 0.230 | 0.226 | 0.223 | 0.225 |
| B | 0.048 | 0.235 | 0.052 | 0.052 | 0.052 | 0.052 | 0.052 | 0.051 | 0.050 | 0.050 | 0.051 | 0.051 |
| C | 0.049 | 0.246 | 0.075 | 0.115 | 0.167 | 0.216 | 0.245 | 0.247 | 0.245 | 0.235 | 0.237 | 0.240 |
| D | 0.049 | 0.248 | 0.076 | 0.117 | 0.175 | 0.221 | 0.241 | 0.243 | 0.242 | 0.237 | 0.237 | 0.250 |
| E | 0.049 | 0.250 | 0.234 | 0.241 | 0.245 | 0.243 | 0.244 | 0.245 | 0.244 | 0.242 | 0.245 | 0.246 |
| F | 0.049 | 0.252 | 0.236 | 0.241 | 0.242 | 0.245 | 0.245 | 0.242 | 0.244 | 0.243 | 0.244 | 0.238 |
| G | 0.049 | 0.245 | 0.076 | 0.154 | 0.230 | 0.247 | 0.241 | 0.237 | 0.237 | 0.239 | 0.234 | 0.240 |
| H | 0.048 | 0.217 | 0.082 | 0.172 | 0.238 | 0.244 | 0.237 | 0.232 | 0.230 | 0.232 | 0.233 | 0.233 |

The optical density was higher for the positive control than for the other conditions, with a mean value of 0.242 for positive control and 0.049 for negative control.

TABLE 3b

| Percentage of inhibition, *C. acnes*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | T− | T+ | 98.3 | 99.3 | 99.9 | 57.4 | 8.2 | 8 | 6.1 | 8 | 9 | 8 |
| B | | | 98.3 | 98.3 | 98.3 | 98.3 | 98.3 | 98.8 | 99.3 | 99.3 | 98.8 | 98.8 |
| C | | | 86.4 | 65.7 | 38.8 | 13.4 | 0 | 0 | 0 | 3.6 | 2.5 | 1.0 |
| D | | | 85.9 | 64.6 | 34.6 | 10.8 | 0.4 | 0 | 0 | 2.5 | 2.5 | 0 |
| E | | | 4.1 | 0 | 0 | 0 | 0 | 0 | 0 | 0 | 0 | 0 |
| F | | | 3.0 | 0 | 0 | 0 | 0 | 0 | 0 | 0 | 0 | 2.0 |
| G | | | 85.9 | 45.5 | 6.1 | 0 | 0 | 2.5 | 2.5 | 1.5 | 4.1 | 1.0 |
| H | | | 82.8 | 36.2 | 2.0 | 0 | 2.5 | 5.1 | 6.1 | 5.1 | 4.6 | 3.6 |

The vehicle (Activolo3-75%) had an antibacterial effect of *P. acnes* when it was used pure up to diluted 1/4. At the dilution 1/16, the vehicle has no antibacterial effect. The results obtained on Ciprofloxacin (as the same dosage) were similar with 99% of inhibition.

The results obtained on the *Mangifera indica* extract (2%) and Pool *Mangifera* (2%) testified an antibacterial effect against *P. acnes*, whereas Pool Mangiferin has no antibacterial effect.

Figure 9:
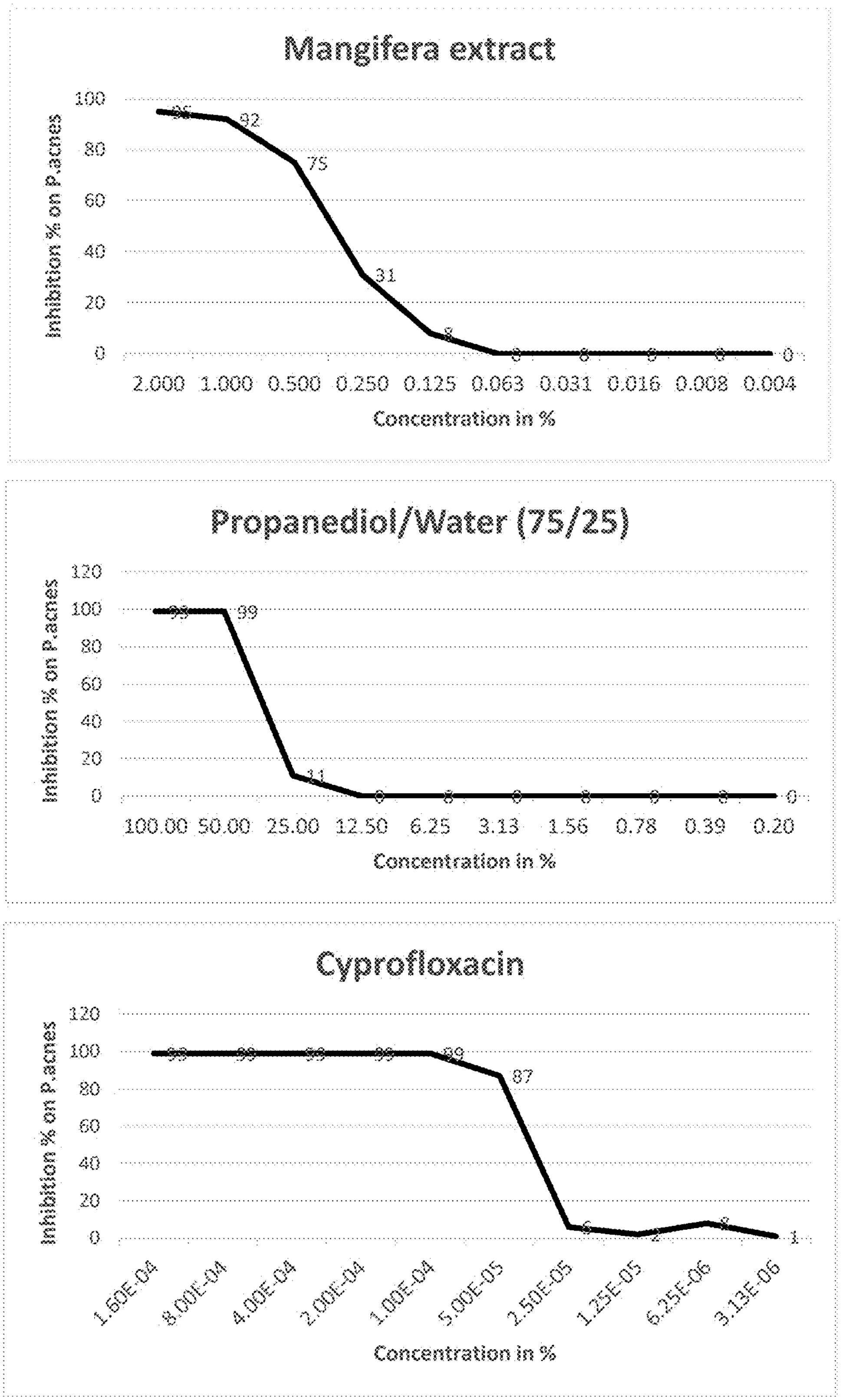
FIG. 9 shows that *Mangifera indica* extract (top) has an anti-bacterial effect from 1% up to 2% with >90% of inhibition. The solvent as such is efficient up to 25% (middle). Ciprofloxacin has an antibacterial effect from $1\times10^{-4}$% with 99% of inhibition (bottom).

The inhibition of *P. acnes* by *Mangifera indica* extract, the solvent (propanediol/water 75/25) and the antibiotic ciprofloxacin is also shown in FIG. 9. *Mangifera indica* extract (FIG. 9 top) has an anti-bacterial effect from 1% up to 2% with >90% of inhibition. The solvent as such is efficient up to 25% (FIG. 9 middle). Ciprofloxacin has an antibacterial effect from $1\times10^{-4}$% with 99% of inhibiion (FIG. 9 bottom).

*C. granulosum*, Bacterial suspension concentration: $1.62 \cdot 10^6$ CFU/ml

TABLE 4a

| Optical density, *C. granulosum*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0.055 | 0.51 | 0.051 | 0.051 | 0.054 | 0.193 | 0.367 | 0.432 | 0.469 | 0.509 | 0.536 | 0.559 |
| B | 0.049 | 0.528 | 0.052 | 0.051 | 0.051 | 0.051 | 0.051 | 0.061 | 0.061 | 0.061 | 0.055 | 0.057 |
| C | 0.049 | 0.539 | 0.077 | 0.093 | 0.253 | 0.416 | 0.492 | 0.532 | 0.548 | 0.561 | 0.555 | 0.537 |
| D | 0.049 | 0.557 | 0.076 | 0.093 | 0.280 | 0.406 | 0.490 | 0.544 | 0.550 | 0.562 | 0.561 | 0.537 |
| E | 0.049 | 0.564 | 0.398 | 0.419 | 0.457 | 0.478 | 0.520 | 0.545 | 0.558 | 0.570 | 0.561 | 0.539 |
| F | 0.048 | 0.56 | 0.391 | 0.417 | 0.449 | 0.479 | 0.505 | 0.545 | 0.592 | 0.573 | 0.561 | 0.546 |
| G | 0.049 | 0.554 | 0.062 | 0.129 | 0.353 | 0.451 | 0.482 | 0.517 | 0.563 | 0.558 | 0.552 | 0.530 |
| H | 0.049 | 0.574 | 0.069 | 0.153 | 0.381 | 0.473 | 0.506 | 0.538 | 0.580 | 0.582 | 0.561 | 0.541 |

The optical density was higher for the positive control than for the other conditions, with a mean value of 0.548 for positive control and 0.050 for negative control.

TABLE 4b

| Percentage of inhibition, *C. granulosum*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | T− | T+ | 99.7 | 99.7 | 99.1 | 71.2 | 36.3 | 23.3 | 15.9 | 7.9 | 2.5 | 0.0 |
| B | | | 99.5 | 99.7 | 99.7 | 99.7 | 99.7 | 97.8 | 97.8 | 97.8 | 99.0 | 98.5 |
| C | | | 94.5 | 91.3 | 59.2 | 26.5 | 11.3 | 3.3 | 0 | 0 | 0 | 2.3 |
| D | | | 94.7 | 91.3 | 53.8 | 28.5 | 11.7 | 0.9 | 0 | 0 | 0 | 2.3 |
| E | | | 30.1 | 25.9 | 18.3 | 14.1 | 5.7 | 0.7 | 0 | 0 | 0 | 1.9 |
| F | | | 31.5 | 26.3 | 19.9 | 13.9 | 8.7 | 0.7 | 0 | 0 | 0 | 0.5 |
| G | | | 97.5 | 84.1 | 39.2 | 19.5 | 13.3 | 6.3 | 0 | 0 | 0 | 3.7 |
| H | | | 96.1 | 79.3 | 33.5 | 15.1 | 8.5 | 2.1 | 0 | 0 | 0 | 1.5 |

The vehicle (Activolo3-75%) had an antibacterial effect on *C. granulosum*, when used pure up to diluted 1/4. At the dilution 1/32, the vehicle has no antibacterial effect. The results obtained on Ciprofloxacin (at the same dosage) were similar with 99% of inhibition.

The results obtained on *Mangifera indica* extract (2%, 1%) and Pool *Mangifera* (2%, 1%) testified an antibacterial effect against *C. granulosum*, whereas Pool Mangiferin has a slight antibacterial effect at 2%.

*S. aureus*: Bacterial suspension concentration: $1.10 \cdot 10^6$ CFU/ml

TABLE 5a

| Optical density, *S. aureus*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0.046 | 0.411 | 0.051 | 0.049 | 0.259 | 0.279 | 0.307 | 0.332 | 0.367 | 0.377 | 0.392 | 0.402 |
| B | 0.046 | 0.412 | 0.047 | 0.053 | 0.053 | 0.048 | 0.048 | 0.048 | 0.048 | 0.048 | 0.048 | 0.048 |
| C | 0.046 | 0.395 | 0.268 | 0.292 | 0.322 | 0.319 | 0.353 | 0.390 | 0.415 | 0.415 | 0.422 | 0.398 |
| D | 0.046 | 0.381 | 0.259 | 0.301 | 0.291 | 0.310 | 0.354 | 0.375 | 0.405 | 0.398 | 0.413 | 0.386 |
| E | 0.046 | 0.397 | 0.327 | 0.348 | 0.359 | 0.368 | 0.367 | 0.364 | 0.378 | 0.369 | 0.366 | 0.392 |
| F | 0.046 | 0.384 | 0.320 | 0.346 | 0.363 | 0.370 | 0.368 | 0.370 | 0.377 | 0.365 | 0.384 | 0.387 |
| G | 0.046 | 0.399 | 0.258 | 0.276 | 0.338 | 0.369 | 0.389 | 0.408 | 0.430 | 0.366 | 0.375 | 0.396 |
| H | 0.046 | 0.402 | 0.270 | 0.286 | 0.317 | 0.350 | 0.391 | 0.402 | 0.404 | 0.391 | 0.395 | 0.405 |

The optical density was higher for the positive control than for the other conditions, with a mean value of 0.398 for positive control and 0.046 for negative control.

TABLE 5b

| Percentage of inhibition, *S. aureus*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | T− | T+ | 98.6 | 99.1 | 39.4 | 33.7 | 25.8 | 18.7 | 8.7 | 5.9 | 1.6 | 0 |
| B | | | 99.7 | 98.0 | 98.0 | 99.4 | 99.4 | 99.4 | 99.4 | 99.4 | 99.4 | 99.4 |
| C | | | 36.9 | 30.0 | 21.5 | 22.4 | 12.7 | 2.2 | 0 | 0 | 0 | 0 |
| D | | | 39.4 | 27.5 | 30.3 | 24.9 | 12.4 | 6.4 | 0 | 0 | 0 | 3.3 |
| E | | | 20.1 | 14.1 | 11.0 | 8.4 | 8.7 | 9.6 | 5.6 | 8.1 | 9.0 | 1.6 |
| F | | | 22.1 | 14.7 | 9.8 | 7.9 | 8.4 | 7.9 | 5.9 | 9.3 | 3.9 | 3.0 |
| G | | | 39.7 | 34.6 | 17.0 | 8.1 | 2.5 | 0 | 0 | 9.0 | 6.4 | 0.5 |
| H | | | 36.3 | 31.7 | 22.9 | 13.5 | 1.9 | 0 | 0 | 1.9 | 0.7 | 0 |

The vehicle (Activolo3-75%) had an antibacterial effect on *S. aureus*, when used pure up to diluted 1/8. At the dilution 1/64, the vehicle has no antibacterial effect. The results obtained on Ciprofloxacin (as the same dosage) were similar with 99% of inhibition.

The results obtained on the active ingredient (*Mangifera* 2%), Pool *Mangifera* (2%) and Pool Mangiferin (2%) testified a slight antibacterial effect.

*H. influenza*: Bacterial suspension concentration: $1.16 \cdot 10^6$ CFU/ml

TABLE 6a

| Optical density, *H. influenza*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 0.054 | 0.177 | 0.058 | 0.056 | 0.055 | 0.119 | 0.162 | 0.185 | 0.194 | 0.183 | 0.180 | 0.185 |
| B | 0.055 | 0.197 | 0.057 | 0.057 | 0.058 | 0.057 | 0.059 | 0.056 | 0.055 | 0.055 | 0.055 | 0.055 |
| C | 0.05 | 0.193 | 0.123 | 0.156 | 0.161 | 0.191 | 0.194 | 0.189 | 0.184 | 0.182 | 0.185 | 0.190 |
| D | 0.05 | 0.19 | 0.121 | 0.143 | 0.146 | 0.183 | 0.192 | 0.189 | 0.187 | 0.186 | 0.189 | 0.193 |
| E | 0.05 | 0.194 | 0.181 | 0.183 | 0.191 | 0.196 | 0.195 | 0.197 | 0.193 | 0.196 | 0.197 | 0.197 |
| F | 0.05 | 0.195 | 0.184 | 0.190 | 0.193 | 0.189 | 0.187 | 0.185 | 0.180 | 0.185 | 0.188 | 0.190 |
| G | 0.05 | 0.196 | 0.146 | 0.175 | 0.182 | 0.187 | 0.189 | 0.184 | 0.179 | 0.181 | 0.184 | 0.195 |
| H | 0.05 | 0.199 | 0.153 | 0.169 | 0.187 | 0.203 | 0.201 | 0.201 | 0.189 | 0.193 | 0.196 | 0.203 |

The optical density was higher for the positive control than for the other conditions, with a mean value of 0.192 for positive control and 0.055 for negative control.

TABLE 6b

| Percentage of inhibition, *H. influenza*: | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | T− | T+ | 97.6 | 99.0 | 99.7 | 53.4 | 22.2 | 5.5 | 0 | 7.0 | 9.1 | 5.5 |
| B | | | 98.3 | 98.3 | 97.6 | 98.3 | 96.8 | 99.0 | 99.7 | 99.7 | 99.7 | 99.7 |
| C | | | 50.5 | 26.5 | 22.9 | 1.2 | 0.0 | 2.6 | 6.3 | 7.7 | 5.5 | 1.9 |
| D | | | 51.9 | 36.0 | 33.8 | 7.0 | 0.5 | 2.6 | 4.1 | 4.8 | 2.6 | 0 |
| E | | | 8.4 | 7.0 | 1.2 | 0 | 0 | 0 | 0 | 0 | 0 | 0 |
| F | | | 6.3 | 1.9 | −0.3 | 2.6 | 4.1 | 5.5 | 9.1 | 5.5 | 3.4 | 1.9 |
| G | | | 33.8 | 12.8 | 7.7 | 4.1 | 2.6 | 6.3 | 9.9 | 8.4 | 6.3 | 0 |
| H | | | 28.7 | 17.1 | 4.1 | 0 | 0 | 0 | 2.6 | 0 | 0 | 0 |

The vehicle had an antibacterial effect on *H. influenza* when used pure up to diluted 1/8. At the dilution 1/32, the vehicle has no antibacterial effect. The results obtained on Ciprofloxacin (as the same dosage) were similar with 99% of inhibition.

The results obtained on the *Mangifera indica* extract (2%) and Pool *Mangifera* (2%) testified an antibacterial effect against *H. influenza*, whereas Pool Mangiferin has no antibacterial effect.

Overall, an antibacterial effect against the tested bacteria has been demonstrated for *Mangifera indica* extract, and also the Pool *Mangifera*, containing four active ingredients described above. In contrast, Pool Mangiferin (Mangiferin only) showed lower antibacterial effect or no effect at all.

b) TKC (Time Kill Curve) Determination

*P. acnes* (ATCC 6919) and *C. granulosum* (ATCC 25564) were cultured in reinforced clostridial broth as recommended by ATCC. pH was adjusted at 6.8+/−0.2 (25° C.) (launch of culture at D−2). Each strain was plated on appropriate plate and grown in the appropriate conditions. Colonies were resuspended in 5 mL of PBS to obtain a 0.5 McFarland OD (approximately $1 \cdot 10^8$ cfu/ml). After two days, the bacterial concentrations were adjusted in reinforced clostridial broth to obtain a solution at $1 \cdot 10^6$ CFU/ml ($5 \cdot 10^4$ CFU/well). The different compounds have been added at different concentrations in water (Launch of *P. acnes* Time Kill Curve, Bacteria quantification at D0). Bacteria quantification has been repeated at T+4 h, T+8 h, T+24 h, T+32 h, T+48 h. For bacteria quantification a Colony counter IUL instruments, flash and go model was used.

A Time Kill Curve (TKC) was performed to determine the effect of the active versus placebo on the growth of *Propionibacterium acnes*.

TABLE 7

| expressed Log10 CFU/ml: | | | | | | | |
|---|---|---|---|---|---|---|---|
| Condition | | T0 | T + 4 h | T + 8 h | T + 24 h | T + 32 h | T + 48 h |
| Negative control | | 0 | 0 | 0 | 0 | 0 | 0 |
| Positive control | | 6.0 | 6.2 | 6.3 | 6.6 | 6.7 | 7.8 |
| Placebo | Pure | 6.0 | 1.5 | 0 | 0 | 0 | 0 |
| | Dilution ½ | 6.0 | 0 | 0 | 0 | 0 | 0 |
| | Diltuion ¼ | 6.0 | 6.0 | 5.6 | 6.4 | 6.3 | 7.7 |
| Mangifera | 2% | 6.0 | 3.7 | 3.6 | 3.6 | 3.5 | 2.5 |
| | 1% | 6.0 | 6.2 | 5.8 | 5.7 | 5.2 | 2.7 |
| | 0.5% | 6.0 | 6.2 | 6.0 | 6.0 | 5.8 | 7.7 |
| Pool | 2% | 6.0 | 5.7 | 5.7 | 6.5 | 6.7 | 7.8 |
| Mangiferin | 1% | 6.0 | 6.0 | 5.8 | 6.5 | 6.7 | 7.8 |
| | 0.5% | 6.0 | 6.2 | 5.7 | 6.6 | 6.7 | 7.8 |
| Pool | 2% | 6.0 | 3.6 | 3.6 | 3.6 | 3.6 | 2.5 |
| Mangifera | 1% | 6.0 | 5.7 | 5.0 | 6.0 | 6.2 | 2.7 |
| | 0.5% | 6.0 | 5.9 | 5.4 | 6.6 | 6.7 | 7.8 |
| Reference (Ciprofloxacin) | 0.5 μg/ml | 6.0 | 0 | 0 | 0 | 0 | 0 |

Figure 10A:
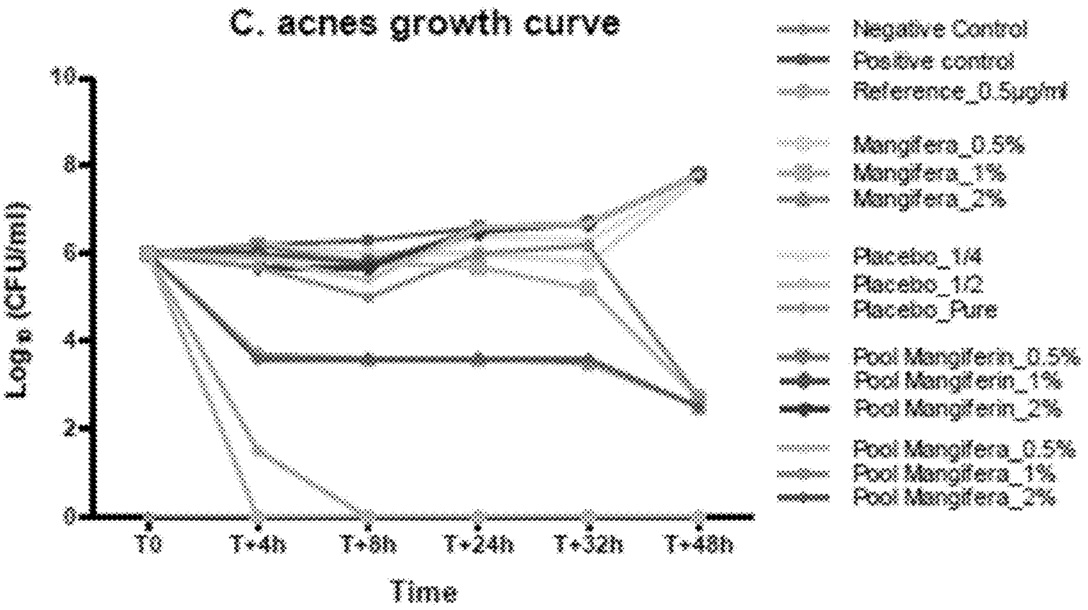
FIG. 10*a* shows *C. acnes* growth curve.
Figure 10B:
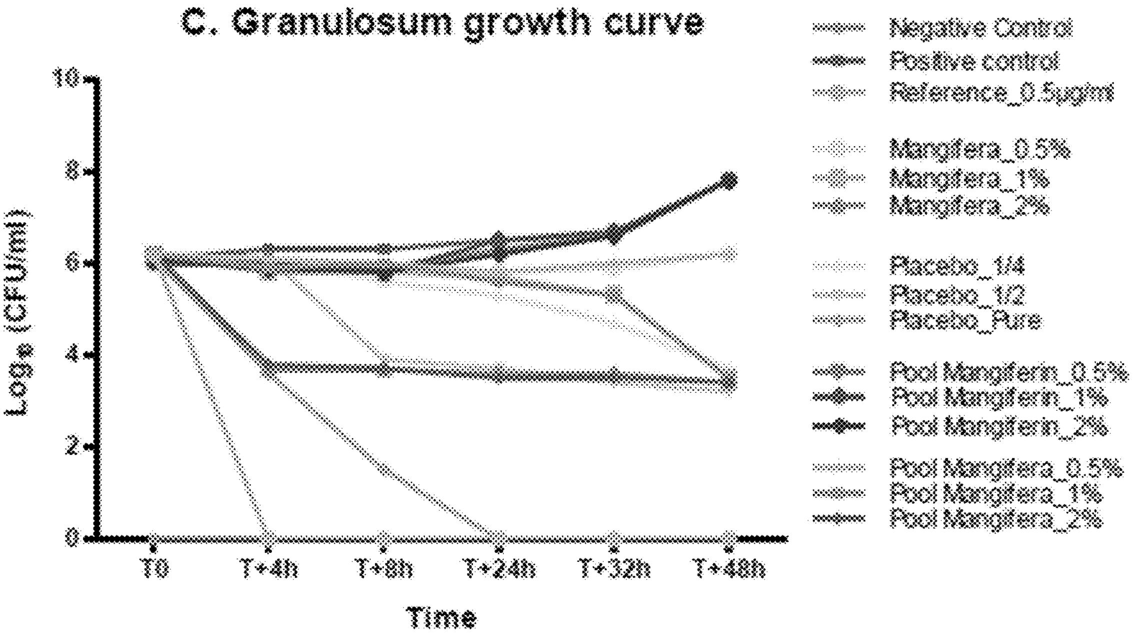
FIG. 10*b* shows *C. Granulosum* growth curve.

From Table 7 and FIG. 10*a* the following can be concluded:

The profile of positive control (*P. acnes* untreated) was stable from T0 to T+24 h, and then bacterial concentration increased from T+32 h to T+48 h. Ciprofloxacin reference induced a decrease of the bacterial growth from T+4 h to T+48 h for each dosage tested.

The cultures treated with the placebo (Activonol-3 at 75%, 1,3-propanediol) diluted (solvent=water) at % and the *Mangifera indica* extract (*Mangifera*) at 0.5% were stable from T0 to T+24 h, and the bacterial concentrations increased from T+32 h to T+48 h. These profiles were close to that of the positive control, testifying no effect on *P. acnes* growth.

Example 9. Clinical Investigation—Impact of *Mangifera indica* Extract on Skin of Caucasian Volunteers The studies have been conducted in double blind and placebo controlled conditions.

a) Panel Description 30 women (aged between 18 and 45 years old, mean age: 30.7±5.8 years) with oily skin (sebum>140 μg/cm$^2$ at the forehead) were divided in two groups of 15 volunteers. Volunteers applied a cream containing 1% of *Mangifera indica* extract or placebo cream (see Table 9 for full compositions) twice a day for 28 days. Samples or measurements were taken at D0, DD14 and D28.

b) INCI Formula

TABLE 9

| INCI Name | Placebo in % (w/v) | Cream or Active in % (w/v) |
|---|---|---|
| AQUA/WATER | 89.30 | 88.30 |
| CETYL ALCOHOL, GLYCERYL STEARATE, PEG-75 STEARATE, CETETH-20, STEARETH-20 | 5.0 | 5.0 |
| ISODECYL NEOPENTANOATE | 4.5 | 4.5 |
| MANGIFERA INDICA (MANGO) LEAF EXTRACT, PROPANEDIOL, WATER (AQUA) | 0 | 1.0 |
| PHENOXYETHANOL | 0.695 | 0.695 |
| DIMETHICONE | 0.3 | 0.3 |
| PHENOXYETHANOL, METHYL PARABEN, PROPYL PARABEN, ETHYL PARABEN | 0.105 | 0.105 |
| FRAGRANCE | 0.1 | 0.1 |

c) Method—Sebum Content

Sebum content is measured by Sebumeter®, a device composed of a box and a cassette. The cassette consists of a frosted film (matte and translucent). The cassette (film) is brought into contact with the area of interest for 30 seconds. The cassette is then inserted into the box, which measures the transparency of the film through transmitted light and determines the sebum rate. In this study, 3 measurements around cheek and nose on left hemi-face were taken.

Measurements were taken on the forehead on day 0 to select and include the volunteers in the study with a sebum level greater than 140 μg/cm$^2$ considered as oily.

d) Results—Sebum Content

Figure 11:
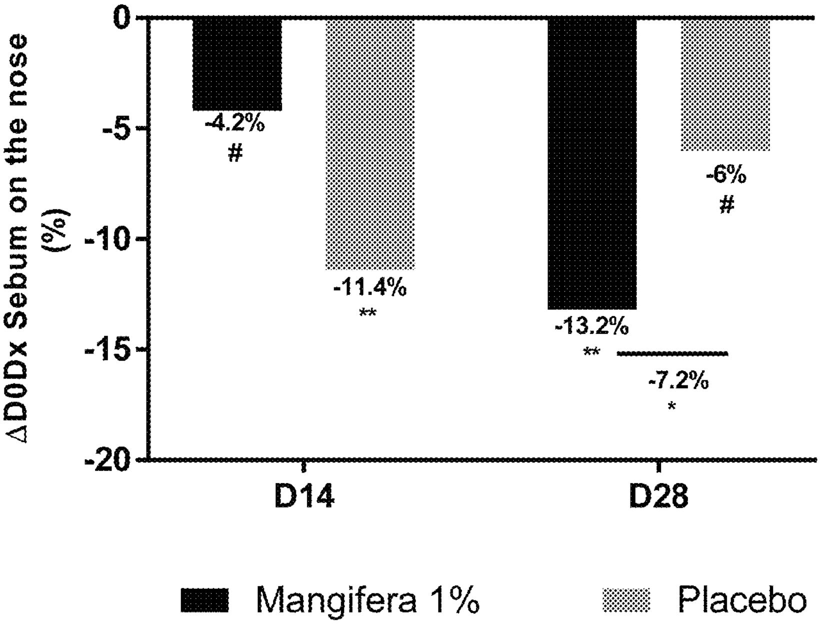
FIG. 11 shows sebum analysis by Sebumeter® after 14 and 28 days of application of cream containing *Mangifera indica* extract at 1% or placebo on Caucasian volunteers.

The evolution of sebum level on oily skin area (cheek and nose area) was analysed. FIG. 11 shows sebum analysis by Sebumeter® after 14 and 28 days of application of cream containing *Mangifera indica* extract at 1% or placebo on Caucasian volunteers. The results are expressed as ΔD0Dx Sebum in the nose.

After 14 days of application, a reduction of sebum with *Mangifera indica* extract and placebo with a higher efficiency for the placebo was observed. After 28 days of application, a significant reduction of sebum by −13.2% with *Mangifera indica* extract was observed, while the placebo formula only reduced it by −6%. In addition, a significant difference between placebo and active was shown, demonstrating that *Mangifera indica* extract at 1% induced a significant reduction of sebum production after 28 days by −7.2% in comparison with placebo on Caucasian skin.

Illustrative pictures taken by VISIA® CR2.3 show that the skin in cheek and nose area appears less oily after 28 days of application of cream containing *Mangifera indica* extract at 1% in comparison to skin treated with the placebo.

e) Method—Porphyrin Reduction Using VISIA® CR2.3

Through Visia® CR 2.3 from Canfield® imaging systems, digital photography of the face was done at different times with repositioning at D0. The control of the repositioning takes place directly on data-processing screen using an overlay visualization of the images at each time of acquisition. The Visia® CR 2.3 allows taking pictures with different types of illuminations and a very rapid capture of images. A series of photos taken under multi-spectral imaging and analysis allow capturing visual information affecting appearance of the skin. The photos were made from front and side.

f) Results—Porphyrin Reduction

Figure 12:
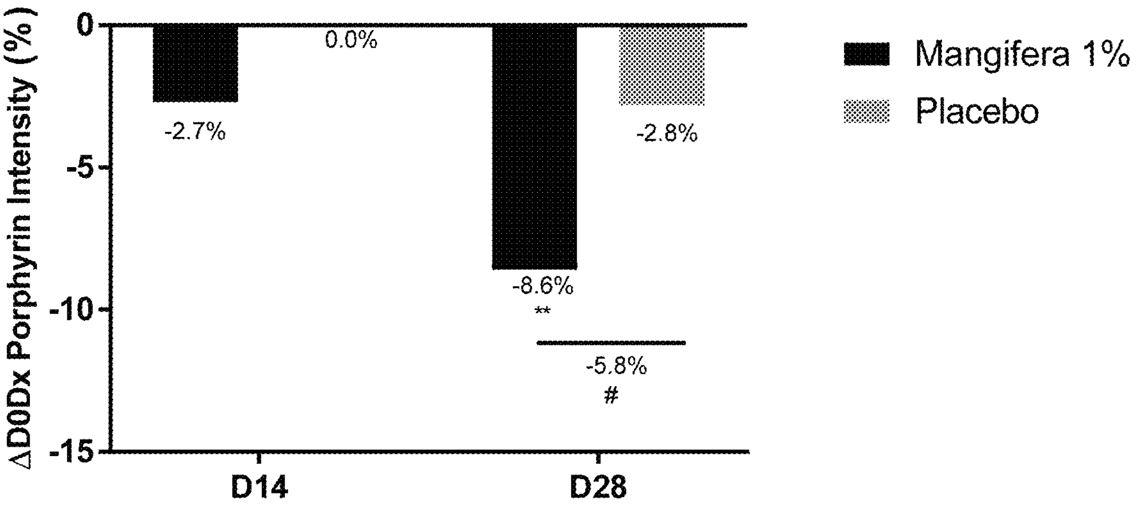
FIG. 12 shows porphyrin intensity analysis by VISIA® CR 2.3 after 28 days of application of cream containing *Mangifera indica* extract at 1% or placebo on Caucasian volunteers on full face.

In this study, the impact of *Mangifera indica* extract on porphyrin intensity was analysed, which can be directly related to the skin microbiota, and in particular to *C. acnes*, known to express porphyrin. *C. acnes* is using sebum to grow. So an excess of sebum is linked to significant porphyrin detection. A reduction of sebum is causing a reduction of observed porphyrin intensity, reflecting an impact on skin microbiota. It was evaluated the full face or localised skin area (cheek and nose) after 28 days of application. FIG. 12 shows porphyrin intensity analysis by VISIA® CR 2.3 after 28 days of application of cream containing *Mangifera indica* extract at 1% or placebo on Caucasian volunteers on full face. The results are expressed as ΔD0Dx Porphyrin intensity. The results demonstrate reduction of porphyrin intensity by −2.7% and −8.6% after 14 and 28 days of application with *Mangifera indica* extract at 1%. In contrast, the placebo didn't evidence any significant results after 14 days and 28 days.

Interestingly, a significant difference between *Mangifera indica* extract at 1% and placebo after 28 days of application with −5.8% demonstrated that *Mangifera indica* extract was able to significantly reduce porphyrin on oily skin on full face.

Figure 13:
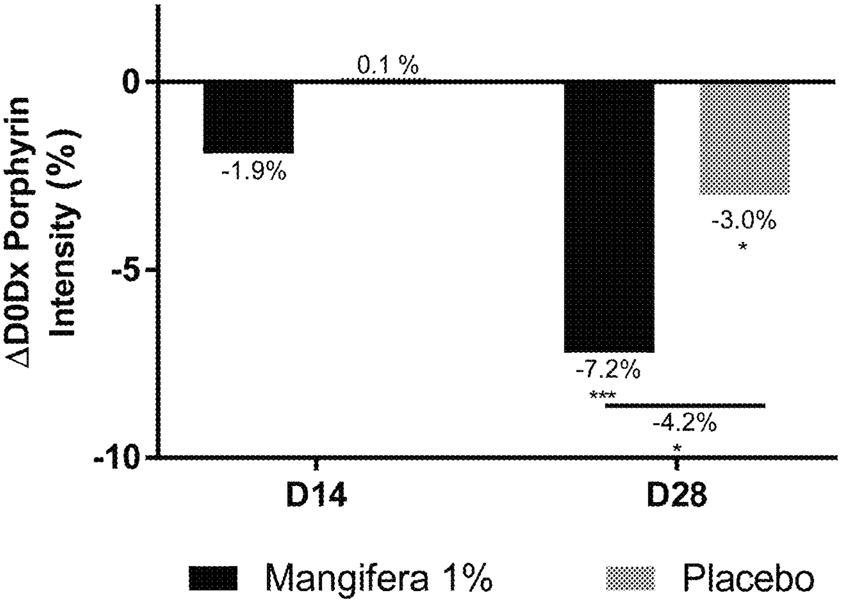
FIG. 13 shows porphyrin intensity analysis by VISIA® CR 2.3 after 28 days of application of cream containing *Mangifera indica* extract at 1% or placebo on Caucasian volunteers on cheek and nose area.

FIG. 13 shows porphyrin intensity analysis by VISIA® CR 2.3 after 28 days of application of cream containing *Mangifera indica* extract at 1% or placebo on Caucasian volunteers on cheek and nose area. The results are expressed as ΔD0Dx Porphyrin intensity. The results demonstrate reduction of porphyrin intensity by −1.9% and −7.2% after 14 and 28 days of application with *Mangifera indica* extract at 1%. The placebo showed a slight effect only after 28 days of application with −3%.

Interestingly, a significant difference between active and placebo after 28 days of application with −4.2% demonstrate that *Mangifera indica* extract at 1% was able to significantly reduced porphyrin on oily skin on cheek and nose area.

g) Method—Improvement of Skin Barrier by Reducing TEWL

Trans-Epidermal Water Loss (TEWL) is the passive diffusion of water through the stratum corneum from the inside of the body to the outside. Its measurement makes it possible to appreciate the integrity of the barrier function. A probe delimiting a cylindrical chamber in contact with the skin is used to measure the gradient of water vapour established on the cutaneous surface, an open chamber in order to partially overcome variations in environmental conditions. The unit of measurement is $g/m^2/h$. During this study, measurements were taken on the forehead (left).

h) Results—Improvement of Skin Barrier

Figure 14:
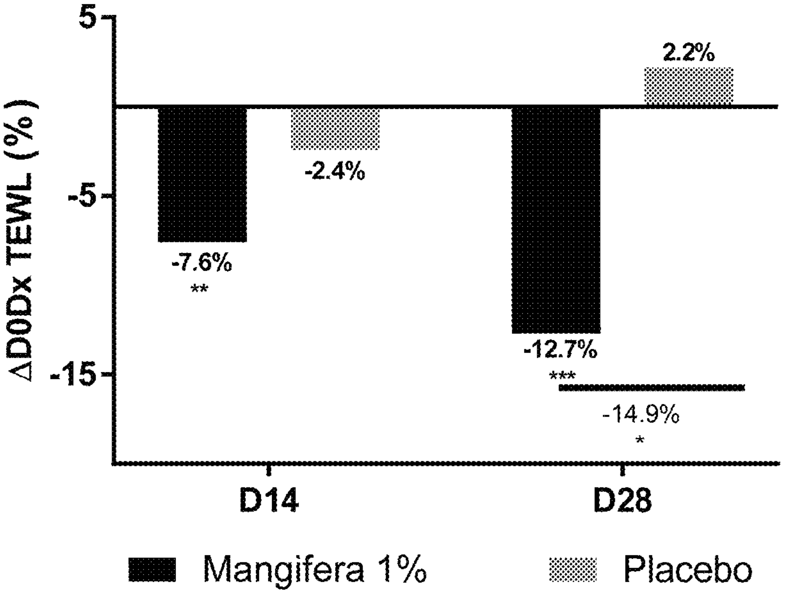
FIG. 14 shows a skin barrier function study by TEWL measurement after 28 days of application of cream containing *Mangifera indica* extract at 1% or placebo on Caucasian volunteers.

FIG. 14 shows a skin barrier function study by TEWL measurement after 28 days of application of cream containing *Mangifera indica* extract at 1% or placebo on Caucasian volunteers. The results are expressed as ΔD0Dx TEWL. It is known that seboregulation product can lead to dry skin and finally disturb the skin barrier function. So the skin barrier by TEWL analysis was studied in order to evaluate the impact of *Mangifera indica* extract.

It was demonstrated that the placebo didn't have any effect on skin barrier either after 14 days nor 28 days. In contrast to this, it was observed that volunteers applying a cream containing *Mangifera indica* extract at 1% show a progressive improvement of skin barrier as observed by the reduction of TEWL by −7.6% and −12.7% after 14 and 28 days, respectively.

There is a significant difference between the both products after 28 days of application showing a difference of −14.9%, demonstrating that *Mangifera indica* extract significantly improves the skin barrier in comparison with placebo after 28 days.

i) Method—Improvement of Sebum Quality Focusing on the Ratio TG/FFA and Oxidized Squalene/Squalene Sebum is composed of Squalene (main lipids), Cholesterol and Free Fatty Acids (FFA), Waxes and Triglycerides (TG). The sebum composition has been studied using GC coupled with MS. A calibration curve was performed on Squalene and Cholesterol, a semi-quantitative analysis was performed for the other biomarkers.

j) Results—Improvement of Sebum Quality Focusing on the Ratio TG/FFA

Sebum was collected during this study and its quality was analysed focusing on the ratio TG/FFA which can reflect some indirect information related to the evolution of skin microbiota and especially on *C. acnes*. Indeed, *C. acnes* consume the TG as a source of energy for its growth releasing FFA following their degradation. Thereby, an impact of TG/FFA ratio could indicate a potential impact on *C. acnes*.

Figure 15:
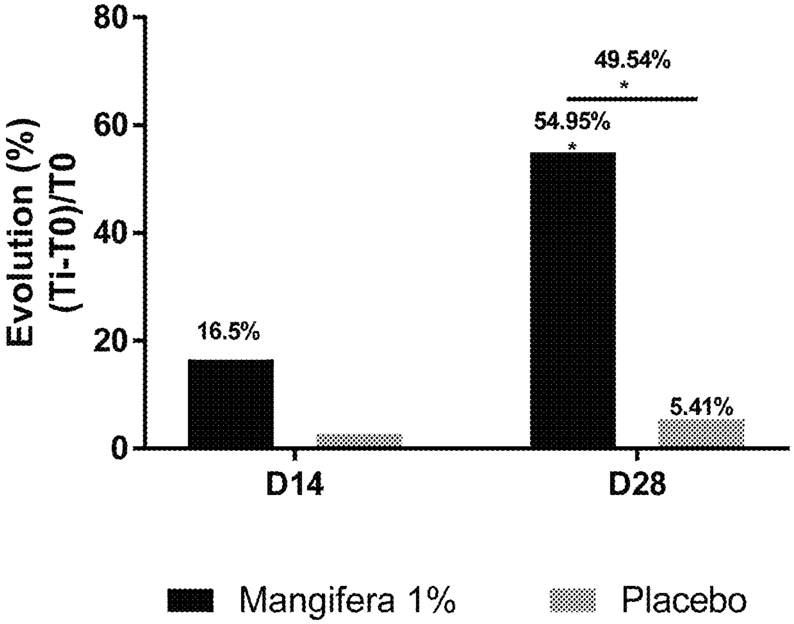
FIG. 15 shows the analysis of TG/FFA ratio from sebum extraction by GC LC/MS after 28 days of application of cream containing *Mangifera indica* extract at 1% or placebo on Caucasian volunteers.

FIG. 15 shows the analysis of TG/FFA ratio from sebum extraction by GC LC/MS after 28 days of application of cream containing *Mangifera indica* extract at 1% or placebo on Caucasian volunteers. The results are expressed as Evolution (%) $(T_i-T_0)/T_0$.

An increase of TG/FFA ratio with time with +16.5% and +54.95% after 14 and 28 days of application of cream containing *Mangifera indica* extract at 1% was demonstrated. The application of a placebo didn't have any effect on this ratio.

Interestingly, a significant difference was shown between the both products after 28 days with +49.5% in favour of the active comprising *Mangifera indica* extract at 1%. This result demonstrates that *Mangifera indica* extract is able to increase the ratio TG/FFA during time significantly, suggesting that the population of *C. acnes* could be impacted by the presence of *Mangifera indica* extract.

Indeed, an increase of TG and a decrease of FFA were observed, suggesting that TG were no more degraded by *C. acnes* as also proven by the reduction of FFA.

k) Results—Improvement of Sebum Quality Focusing on the Ratio Oxidized Squalene/Squalene Also the ratio oxidized squalene (SQOOH)/squalene (SQ) was analysed in the sebum, because in the case of sebum excess it can accumulate oxidized squalene, thereby promoting inflammation of the skin that leads to acne. A study of this ratio is also a way to prove whether *Mangifera indica* extract can improve the quality of the sebum.

Figure 16:
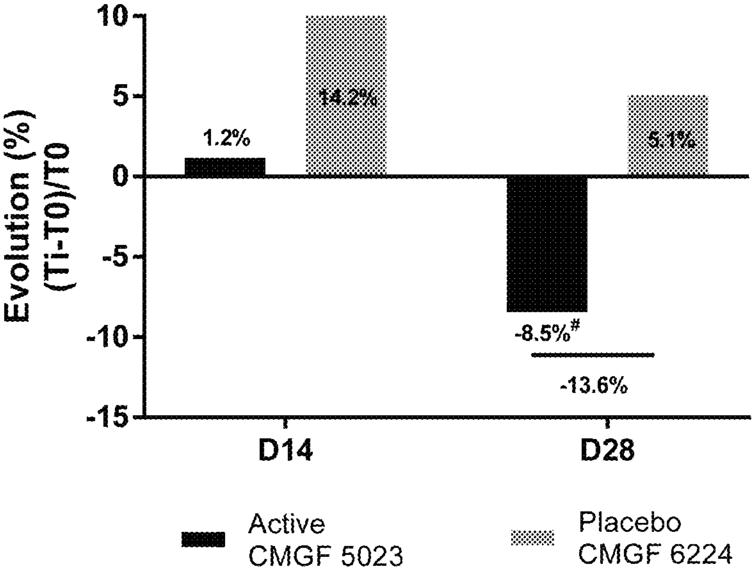
FIG. 16 shows the analysis of SQOOH/SQ ratio from sebum extraction by GC LC/MS after 28 days of application of cream containing *Mangifera indica* extract at 1% or placebo on Caucasian volunteers.

FIG. 16 shows the analysis of SQOOH/SQ ratio from sebum extraction by GC LC/MS after 28 days of application of cream containing *Mangifera indica* extract at 1% or placebo on Caucasian volunteers. The results are expressed as Evolution (%) $(T_i-T_0)/T_0$.

A significant reduction of the ratio SQOOH/SQ was observed after 28 days of application of the cream with *Mangifera indica* extract at 1% while placebo demonstrated the inverse effect with an increase of this ratio over time. This result demonstrated that *Mangifera indica* extract seem to improve the sebum quality by reducing the accumulation of oxidized squalene in the sebum.

Example 10. Metagenomic Analysis a) Microbiota Sampling and Storage

Skin microbiota of the panel described in Example 9a) was also studied during the same clinical evaluation. Samples of microflora were collected from the forehead of 30 volunteers by a non-invasive swabbing method, using sterile swabs moistened with a sterile solution of 0.15 M NaCl. Swabs were transferred at −20° C. and kept frozen until DNA extraction. Sampling was done before treatment (D0), and after 14 (D14) and 28 (D28) days of treatment, using a standardized procedure.

b) DNA Extraction

DNA extraction was performed for each sample using the DNeasy PowerLyzer® PowerSoil® DNA Isolation Kit with Qiacube device (Qiagen, Hilden, Germany), with the following modifications: The tip of each swab was detached with a sterile surgical blade and transferred into a 1.5 mL tube containing 750 μL of Bead Solution. The sampled biomass was suspended by stirring and pipetting, and then transferred to a bead beating tube. The remaining steps were performed according to the manufacturer instructions. DNA concentration was determined using the QuBit dsDNA HS fluorometric quantitation kit (Invitrogen, ThermoFisher Scientific, Courtaboeuf, France) according to the manufacturer instructions.

c) Sequencing and Data Analysis 16S rRNA gene sequencing: Sequencing was performed with the MiSeq device (Illumina, Inc., San Diego, CA, USA) through a 500 cycles paired-end run, targeting the V3V4 16S variable regions using the following primers: 16S-Mi341F forward primer 5'-CCTACGGGNGGCWGCAG-3' and 16S-Mi805R reverse primer 5'-GACTACHVGGGTATCTAATCC-3', producing about 460 bp amplicons.

PCR1s were performed as follows: 8 μL of template DNA (0.2 ng) were mixed with 5 μL of each reverse and forward primers (1 μM), 5 μL of KAPA HiFi Fidelity Buffer (5×), 0.8 μL of KAPA dNTP Mix (10 mM each), 0.7 μL of RT-PCR grade water (Ambion), and 0.6 μL of KAPA HiFi hotstart Taq (1 U/μL), for a total volume of 25 μL. Each amplification was duplicated, and duplicates were pooled after amplification. PCR1 cycles consisted of 95° C. for 3 min and then 32 cycles of 95° C. for 30 s, 59° C. for 30 s, and 72° C. for 30 s, followed by a final extension at 72° C. for 3 min, with a BioRad CFX1000 thermocycler. Negative and positive controls were included in all steps to check for contamination. All duplicate pools were controlled by gel electrophoresis, and amplicons were quantified using fluorometry.

Libraries ready for analysis were then produced following the Illumina guidelines for 16S metagenomics libraries preparation. Briefly, the PCR1 amplicons were purified and controlled using an Agilent 2100 Bioanalyzer (Agilent Technologies, Santa Clara, USA). To enable the simultaneous analysis of multiple samples (multiplexing), Nextera® XT indexes (Illumina) were added during PCR2 using between 15 to 30 ng of PCR1 amplicons. PCR2 cycles consisted of 94° C. for 1 min and then 12 cycles of 94° C. for 60 s, 65° C. for 60 s, and 72° C. for 60 s, followed by a final extension at 72° C. for 10 min. Indexed libraries were purified, quantified and controlled using an Agilent 2100 Bioanalyzer. Validated indexed libraries were pooled in order to obtain an equimolar mixture.

The run (500 cycles) was achieved on MiSeq sequencer (Illumina) using the MiSeq Reagent Kit v3 600 cycles (Illumina). The sequencing run produced an output of 12.7 million of paired-end reads of 250 bases, i.e. up to 3.2 Gigabases. The libraries and the MiSeq run were performed by Givaudan, at the GeT-PlaGe platform (INRA, Auzeville, France).

After the MiSeq run, raw data sequences were demultiplexed and quality-checked to remove all the reads with ambiguous bases. Indexes and primers sequences were removed with cutadapt (v1.9; http://cutadapt.readthedocs.io/en/stable/index.html) and reads with fastq score lower than 28 were trimmed. The forward and reverse sequences were paired using bbmerge (https://jgi.doe.gov/data-and-tools/bbtools/). Samples with less than 5000 paired-sequences were discarded. The remaining paired sequences were then treated using an in-house pipeline that uses vsearch (Rognes et al., 2016) to remove chimeras and amplicons with PCR errors. Sequences were then split into Operational Taxonomic Units (OTUs, a cluster of similar sequence variants of the 16S rRNA marker gene sequence) at a 1% dissimilarity level using swarm (v2.6—Mahe et al., 2015). Unique amplicons were mapped to the SILVA SSU Ref NR 99 (non-redundant) database (release 132; https://www.arb-silva.de/) for taxonomic assignation using the RDP classifier (Wang et al., 2007). Data normalization and analyses were done using R statistical computing environment (v3.2.0; https://www.r-project.org/—R core team (2014) using Bioconductor package (mainly Phyloseq, DESeq2 and Vegan libraries; http://www.bioconductor.org/).

Data were then compared using Wilcoxon's test for paired samples (Wilcoxon, 1945). Due to multiple testing, p-value were adjusted using false discovery rate (FDR) correction (Binyamini and Hochberg, 1995).

d) Results—Impact of the Product on Skin Microbiota Using Metagenomic Analysis

Table 10 shows the evolution of relative abundances of four impacted bacteria genera after 14 or 28 days of application of cream containing *Mangifera indica* extract at 1% (vehicule+active) or placebo (vehicule) on Caucasian volunteers.

After 14 days of placebo application (vehicule), there was observed a significant decrease of *Pseudomonas* (pvalue=0.018) and *Serratia* (pvalue=0.011), and additionally, after 28 days of placebo application, a significant increase of *Acinetobacter* (pvalue=0.038) and *Staphylococcus* (pvalue=0.057). However, during the same period of time, no significant variation of the relative abundances of these four bacteria genera evolved with active treatment (vehicule+active).

TABLE 10

| | Active | | | Placebo | | | Mann |
|---|---|---|---|---|---|---|---|
| | Mean (%) | Average variation (%) vs D 0 | Wilcoxon test versus D 0 | Mean (%) | Average variation (%) vs D 0 | Wilcoxon test versus D 0 | Whitney test versus placebo |
| | *Pseudomonas* | | | | | | |
| D 0 | 1.02 | | | 0.98 | | | NS |
| D 14 | 0.95 | −6.8% | NS | 0.57 | −41.8% | 0.018 | NS |
| | *Serratia* | | | | | | |
| D 0 | 0.18 | | | 0.21 | | | NS |
| D 14 | 0.19 | 5.6% | NS | 0.11 | −47.6% | 0.011 | NS |
| | *Acinetobacter* | | | | | | |
| D 0 | 0.05 | | | 0.10 | | | NS |
| D 28 | 0.04 | −18.2% | NS | 0.45 | 353% | 0.038 | NS |
| | *Staphylococcus* | | | | | | |
| D 0 | 31.8 | | | 17.1 | | | NS |
| D 28 | 34.4 | 8.2% | NS | 23.3 | 36.0% | 0.057 | NS |

NS: not significant

It was shown that the placebo induced some modification of skin microbiota composition leading to dysbiosis (a microbial imbalance) over time. In contrast, the addition of *Mangifera indica* extract at 1% to the vehicule caused a protection of the skin microbiota balance over time. These results evidenced that *Mangifera indica* extract is microbiome friendly, protecting the skin microbiota against vehicule-mediated dysbiosis over time.

Figure 17A:
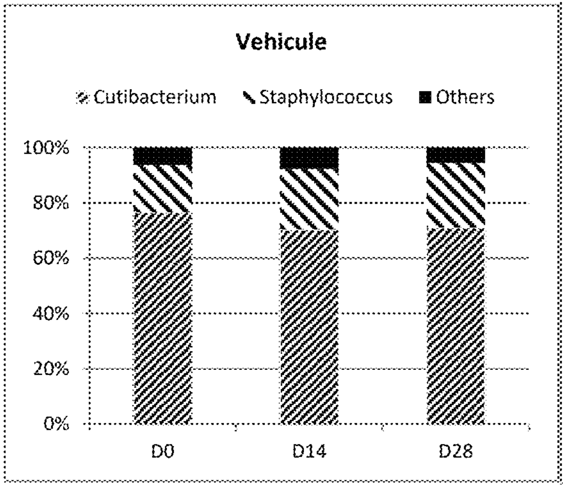
FIG. 17*a* shows a representation of skin microbiota composition over time after treatment with placebo (vehicule) for 28 days analysis by metagenomic.
Figure 17B:
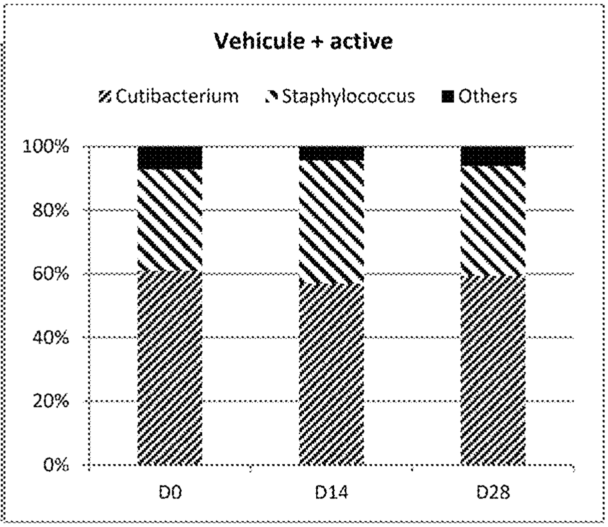
FIG. 17*b* shows a representation of skin microbiota composition over time after treatment with *Mangifera indica* extract at 1% (vehicule+active) for 28 days analysis by metagenomic.

FIG. 17 shows a representation of skin microbiota composition over time after treatment with placebo (vehicule FIG. 17*a*) and *Mangifera indica* extract at 1% (vehicule+active, FIG. 17*b*) for 28 days analysis by metagenomic.

Example 11. Clinical Investigation—Impact of *Mangifera indica* Extract on Skin of Asian Volunteers a) Panel Description This study has been conducted in double blind and placebo controlled conditions. 40 women (aged between 18 and 45 years old, mean age: 30.5 years) with oily skin (sebum>100 μg/cm$^2$ at the forehead) were divided in two groups of volunteers. Volunteers applied a cream containing 2% of *Mangifera indica* extract or placebo cream (see Table 11 for full compositions)) twice a day for 28 days. At D0, D14 and D28, we analysed the sebum quantity using Sebumeter® and take illustrative pictures by VISIA®.

b) INCI Formula

TABLE 11

| INCI Name | Placebo in % (w/v) | Cream or Active in % (w/v) |
|---|---|---|
| AQUA/WATER | 89.30 | 88.30 |
| CETYL ALCOHOL, GLYCERYL STEARATE, PEG-75 STEARATE, CETETH-20, STEARETH-20 | 5.0 | 5.0 |
| ISODECYL NEOPENTANOATE | 4.5 | 4.5 |
| MANGIFERA INDICA (MANGO) LEAF EXTRACT, PROPANEDIOL, WATER (AQUA) | 0 | 2.0 |
| PHENOXYETHANOL | 0.695 | 0.695 |
| DIMETHICONE | 0.3 | 0.3 |

TABLE 11-continued

| INCI Name | Placebo in % (w/v) | Cream or Active in % (w/v) |
|---|---|---|
| PHENOXYETHANOL, METHYL PARABEN, PROPYL PARABEN, ETHYL PARABEN | 0.105 | 0.105 |
| FRAGRANCE | 0.1 | 0.1 |

c) Method—Sebum Content

Sebum content is measured by Sebumeter®, as described in Example 9c.

Measurements were taken on the forehead on day 0 to select and include the volunteers in the study with a sebum level greater than 100 μg/cm$^2$ considered as oily.

d) Results—Sebum Content

Figure 18:
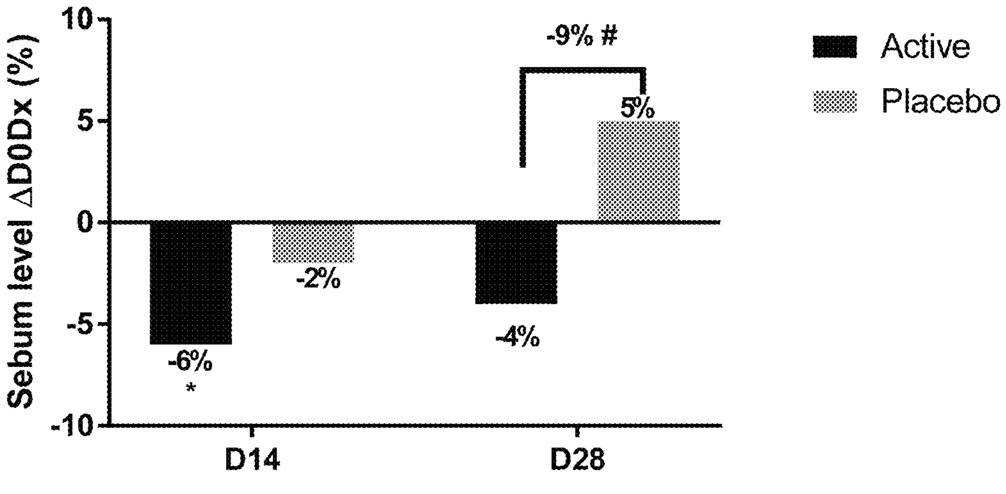
FIG. 18 shows sebum analysis by Sebumeter® after 14 and 28 days of application of cream containing *Mangifera indica* extract at 2% or placebo on Asian volunteers.

The evolution of sebum level on oily skin area (cheek and nose area) was analysed. FIG. 18 shows sebum analysis by Sebumeter® after 14 and 28 days of application of cream containing *Mangifera indica* extract at 2% or placebo on Asian volunteers. The results are expressed as Sebum level ΔD0Dx (%).

The results show that *Mangifera indica* extract at 2% caused significant reduction of sebum of −6% after 14 days, which is maintained until 28 days showing a reduction of −4%. In the same time, the placebo does not cause any significant difference on sebum level, but it even seems to slightly increase the sebum after 28 days. In comparison with placebo, the active significantly reduced the sebum production after 28 days of application by −9%.

Illustrative pictures taken by VISIA® CR2.3 show that the skin in cheek and nose area appears less oily after 28 days of application of cream containing *Mangifera indica* extract at 2% in comparison to skin treated with the placebo.

Example 12. Clinical Investigation—Impact of *Mangifera indica* Extract on Skin of African Volunteers a) Panel Description This study has been conducted in double blind and placebo controlled conditions.

40 women (aged between 18 at 45 years old) with oily skin (sebum level>140 μg·cm$^2$ on forehead) were divided in two groups of 20 volunteers. Volunteers applied a cream containing 2% of *Mangifera indica* extract or placebo cream twice a day for 28 days. At D0, D14 and D28, sebum quantity was analysed using Sebufix®.

a) INCI formula

TABLE 12

| INCI Name | Cream or Active in % (w/v) | Placebo in % (w/v) |
|---|---|---|
| AQUA | 85.1 | 87.1 |
| CETEAYL ALCOHOL | 8 | 8 |
| MANGIFERA INDICA (MANGO) LEAF EXTRACT, PROPANEDIOL, WATER (AQUA) | 2 | 0 |
| GLYCERYL STEARATE PEG-100STEARATE | 2 | 2 |
| PETROLATUM | 1 | 1 |
| PARAFFIN LIQUIDIUM, | 1 | 1 |
| PROPYLENE GLYCOL, DIAZOLIDINYL UREA, METHYLPARABEN, PROPYLPARABEN, | 0.8 | 0.8 |
| CARBOMER | 0.1 | 0.1 |

b) Method—Reduction of Sebum Using Sebufix® Method

Sebufix® F 16 is a special sheet that absorbs sebum from the skin surface thanks to its micro-pores and shows them as spots of different sizes. When mounted on the Visioscan® camera, qualitative sebum production can be uniquely monitored in real time.

Aspect of a computerized image from lipid-sensitive tape. the black dots represent the sebum output at the follicular orifice. With the software the number, size and area covered with spots can be evaluated.

c) Results—Reduction of Sebum

Figure 19:
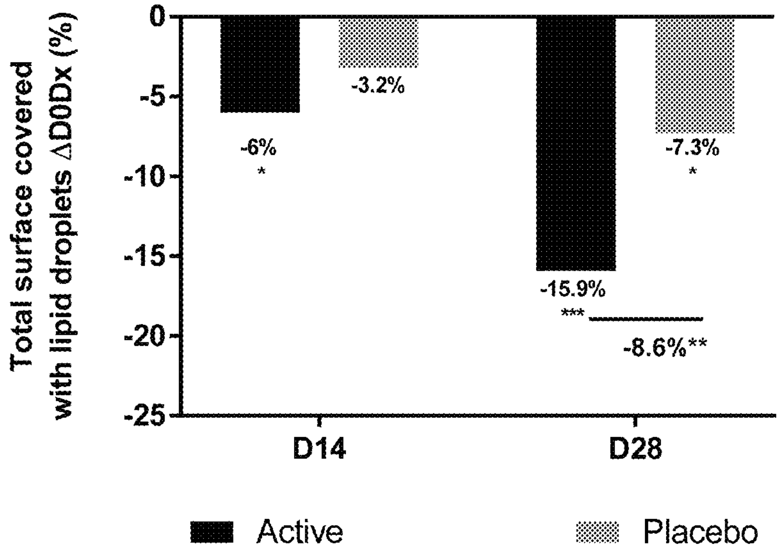
FIG. 19 shows the analysis of total surface covered with lipid droplets after 28 days of application of cream containing *Mangifera indica* extract at 2% or placebo on African volunteers.

FIG. 19 shows the analysis of total surface covered with lipid droplets after 28 days of application of cream containing *Mangifera indica* extract at 2% or placebo on African volunteers. The result is expressed as ΔD0Dx (%).

Using the sebufix method, it was demonstrated that *Mangifera indica* extract significantly reduced the total surface covered by lipid droplets by −6% and −15.9% after 14 and 28 days respectively. The placebo evidenced a slight efficacy as observed by the reduction of total surface covered by lipid droplets by −7.3% after 28 days only.

We observed a significant difference between the both products after 28 days of application demonstrated the efficacy of *Mangifera indica* extract at 2% on sebum reduction on African volunteers showing −8.6%.

Figure 20:
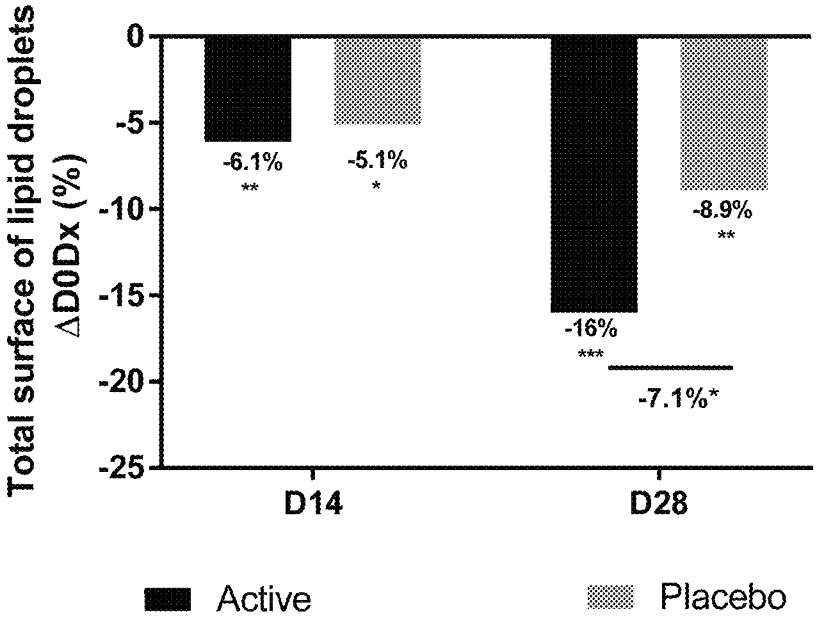
FIG. 20 shows the analysis of total surface of lipid droplets after 28 days of application of cream containing *Mangifera indica* at 2% or placebo on African volunteers.

FIG. 20 shows the analysis of total surface of lipid droplets after 28 days of application of cream containing *Mangifera indica* at 2% or placebo on African volunteers. The result is expressed as ΔD0Dx (%).

So it was also demonstrated that *Mangifera indica* extract significantly reduced the total surface of lipid droplets by −6.1% and −16% after 14 and 28 days respectively.

The placebo evidenced a slight efficacy as observed by the reduction of total surface of lipid droplets by −5.1% and −8.9% after 14 and 28 days respectively.

A significant difference on sebum reduction on African volunteers of −7.1% between the both products after 28 days of application demonstrated the efficacy of *Mangifera indica* extract at 2%.

Example 13. Clinical Investigation—Impact of *Mangifera indica* Extract on Scalp a) Panel Description 46 women (aged between 18 and 58 years old, mean age: 33±2 years) were divided in two groups of volunteers with oily and greasy hair (sebum>60 $\mu g/cm^2$ on the scalp). Volunteers applied a shampoo containing *Mangifera indica* extract at 1% or placebo every two days for 28 days. The sebum level was analysed by Sebumeter® after 14 and 28 days.

b) INCI Formula

TABLE 13

| INCI Name | Placebo in % (w/v) | Shampoo or Active in % (w/v) |
|---|---|---|
| AQUA/WATER | 87.00 | 86.00 |
| SODIUM LAURETH SULFATE | 7.8 | 7.8 |
| COCAMIDOPROPYLBETAINE | 3.6 | 3.6 |
| MANGIFERA INDICA (MANGO) LEAF EXTRACT, PROPANEDIOL, WATER (AQUA) | 0 | 1.0 |
| SODIUM CHLORIDE | 0.5 | 0.5 |
| PHENOXYETHANOL | 0.6 | 0.6 |
| FRAGRANCE | 0.5 | 0.5 |

c) Reduction of Sebum Using Sebumeter®

It is a photometric method. A synthetic ribbon, which becomes transparent when in contact with absorbed lipids, is applied to the measurement zone for precisely 30 seconds. Its transparency increases proportionally with the quantity of sebum from the hydrolipidic film with which it is in contact.

A reflectometry recording is used to quantify the increase of the light transmitted and to determine the total mass of the lipids excreted by the surface unit (in $\mu g/cm^2$).

d) Results

Figure 21:
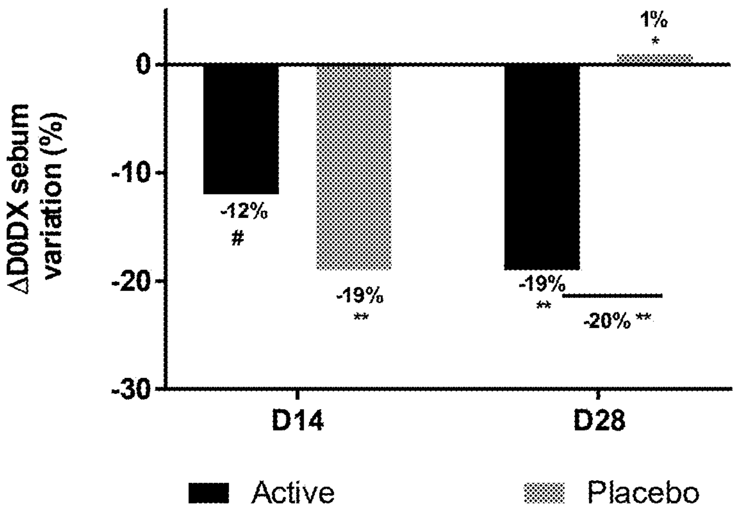
FIG. 21 shows the analysis of Sebum on scalp after shampoo application containing *Mangifera indica* extract at 1% or placebo.

FIG. 21 shows the analysis of Sebum on scalp after shampoo application containing *Mangifera indica* extract at 1% or placebo. The result is expressed as ΔD0Dx sebum variation (%).

It was demonstrated that the shampoo containing 1% of *Mangifera indica* extract significantly reduced the sebum content by −12% and −19% after 14 and 28 days respectively. The placebo evidenced an effect after 14 days of application showing −19% and didn't have any after 28 days, suggesting a potential impact of the usage of new formula but not enough efficient without *Mangifera indica* extract finally.

A significant difference between both products after 28 days of application demonstrated a strong efficacy of *Mangifera indica* extract on the reduction of sebum on oily scalp and hair.

Example 14. In Silico Study—Molecular Docking Study on Mangiferin and PPAR-γ

Based on previous data (example 4), there was emitted the hypothesis that the mangiferin is interacting with PPARγ (PPARG) and in this way disturbs the lipogenesis mechanism by a control of gene expression of some enzymes involving in sebum production.

a) Method

The protein data bank (PDB) database lists numerous crystallographic structures of the ligand binding domain (residues 207 to 476) of PPAR-γ alone, bound to small molecules, in the presence or absence of another partner, RXR-α. Among the interesting structures, the PDB codes 1PRG, 2Q5S and 4F9M have been retained, which have 2.2, 2.05, 1.9 Å resolution, respectively. These targets were prepared with Schrodinger Suite software in order to correct any defects in the structure (protonation states, steric clashes, water molecules/cofactors removal) that could impact the sampling during the molecular docking step.

The ligand structure mangiferin (MGF) corresponds to the one identified in Pubchem. It has also been prepared with Schrodinger Suite software. Conformational search has confirmed that the ligand is flat and does not exhibit a large conformational diversity, leading to a "quite rigid" structure. All docking experiments were focused on the cavity that binds total and partial PPAR-γ agonists. The results obtained show that the quality of the interaction depends on the initial PPAR-γ structure and the presence or absence of a cofactor in the cavity.

Then the interaction energy was quantified with the MM-PBSA method at 3 stages of the simulation (between the 25th and 30th ns, 95th and 100th ns, and finally between 145th and 150th ns of simulation). This method also decomposes the energy contribution of the residues surrounding the binding cavity to the global interaction. The Mean of Energy contribution and standard error are plotted for each residue of PPAR-γ.

b) Results—Prediction of Interaction Between PPARγ and Mangiferin

Figure 22:
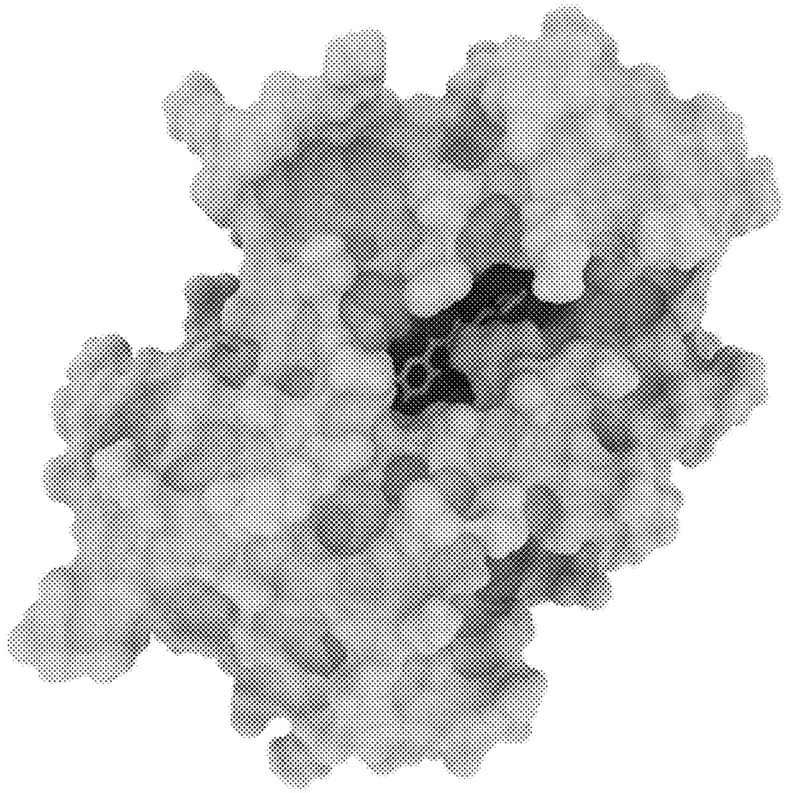
FIG. 22 shows that by using molecular docking method, it was demonstrated that mangiferin was able to bind the PPAR-γ, showing mangiferin in the cavity of PPAR-γ.

By using molecular docking method, it was demonstrated that mangiferin was able to bind the PPAR-γ as presented in FIG. 22, showing mangiferin in the cavity of PPAR-γ.

The binding energy needed to its interaction and also the involved residues have been determined. These parameters are very important to predict if the interaction is probable or not. The lower the binding energy, the more favourable the interaction. It was also analysed if there are residues unfavourable to this interaction, which could predict the stability of the complex.

Figure 23:
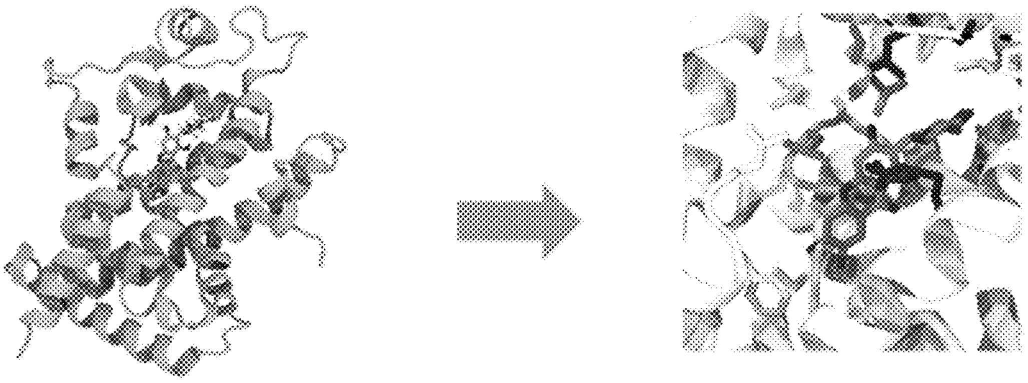
FIG. 23 shows a possible conformation of Mangiferin inside the cavity with favourable interactions.

The results evidence a very low binding energy of −164 kJ/mol indicating that the interaction between the two molecules is possible. Interestingly, no unfavourable residues to the interaction have been identified, suggesting that an interaction is possible without any constraint. FIG. 23 shows a possible conformation of Mangiferin inside the cavity with favourable interactions The stability of the interaction was evaluated using molecular dynamic simulation by in silico method. The distance between residues from the two structures has been observed during interaction for 35 ns of simulation in order to analyse the stability of the interaction.

Figure 24:
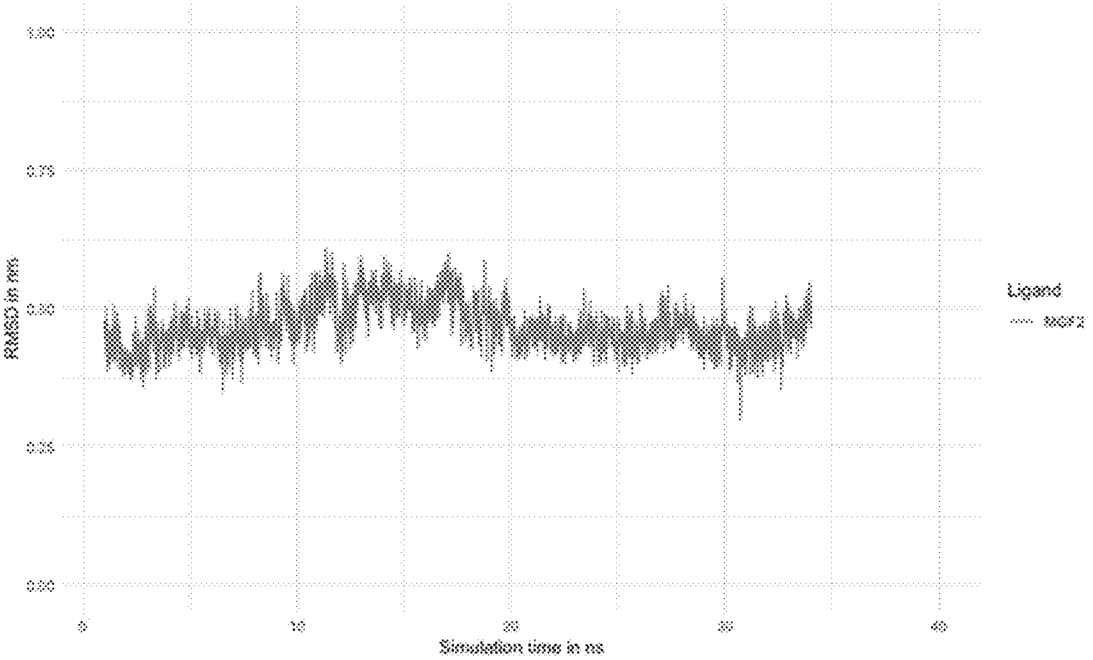
FIG. 24 is an illustration of the result on molecular dynamic method demonstrating the evolution of the distance between residues, the distance between the two structures is totally stable for 35 ns of stimulation.

As shown in FIG. 24, which is an illustration of the result on molecular dynamic method demonstrating the evolution of the distance between residues, the distance between the two structures is totally stable for 35 ns of stimulation.

Using the in silico method, it was demonstrated that the interaction between mangiferin and PPAR-γ is possible and the complex is stable in time. Thereby, the hypothesis can be made that the seboregulation activity of *Mangifera indica* extract would be induced by direct impact of mangiferin with PPAR-γ which is a transcription factor involved in the control of expression of genes coding for enzyme related to sebum production.

Example 15. In Silico Study—Inverse Docking Method on Maclurin and Iriflophenone There was further an interest to predict a potential mechanism explaining how the other molecules of *Mangifera indica* extract, more precisely iriflophenone (ICG) and maclurin (MCG), would be involved in the control lipogenesis.

a) Method

Ligand- and protein-based screening was carried out with Selnergy, an in silico screening tool for biological applications. It allows for searching similar annotated ligands in a database of 1,000,000 known active products and docking the studied molecules on a database of 10,000 protein X-Ray and homology modelling structures. The proteins are annotated for their therapeutic classes, protein classes, organism sources and type of models.

b) Studied Molecule Structures

The 3D structure of iriflophenone (ICG) and maclurin (MCG) has been calculated with XConcord 6.1 from Tripos (MO, USA), and its internal energy has been minimised to have a reasonable conformation.

c) Ligand-Based Approach 1,000,000 ligands were gathered with biological activity annotations, from scientific literatures. Their 3D structures were generated with XConcord 6.1 from Tripos (MO, USA) and their electrostatic and steric properties calculated for comparison with studied compounds. The biological activities were derived from protein binding data, functional or cellular information. Similarities of active ligands and studied molecules are evaluated with their similarity of steric and electrostatic properties with "topomer approach"1 then with pharmacophoric properties with Surflex-sim2. Molecules distant of less than 185 units are considered similar topomer wise and compounds aligned with a score of at least 7 are considered pharmacophorically similar.

d) Protein-Based Approach

Protein 3D structures were obtained from Protein Data Bank (http://www.rcsb.org), the deposit site of crystallographic protein structures, with particular focus on co-crystallised structures with a ligand, so that the binding site is clearly identified. Several 3D structures of the same protein have been used in order to take into account the flexibility of the protein.

e) Validation of the Protein Models

Co-crystallised ligands have been extracted from the 3D structures of the proteins. Then, they are docked, and Selnergy has to find the same position as the experimental ligand position—or the closest ones.

If this step is successful, several other known ligands are docked mixed with "decoy molecules", Selnergy has to discriminate the active from the inactive compounds in terms of interaction energy. The calculated energy of the known ligands will serve as reference for determining energy threshold for possible interactions.

The successful models will be included in Selnergy target database. The unsuccessful ones are further refined (e.g. residue conformation modifications, docking parameters etc.) and revalidated according to the described procedure. If the model is not viable, it is discarded.

F) in Silico Profiling

ICG and MCG were docked with Selnergy on our target database containing 10,000 3D structures. Selnergy proposed 10 conformations for each molecule/protein pair. Figure X shows Selnergy interface for calculation. Furthermore, a ligand-based comparison is performed on the database of 1,000,000 annotated ligands based on structure-activity relationship.

g) Post-Processing of the Virtual Hits

In order to focus on molecules with a significantly outstanding estimated binding energy compared to the average value, the following score has been used:

$$\text{Score} \geq \bar{A} + k \cdot \sigma$$

With:

$\bar{A}$: the mean of score for a particular compound;

k: constant depending of the confidence level desired; depending on the number of results; with this score, it may be used:

k=1.04 for 70% of confidence;

k=1.65 for 90% of confidence; or k=6 for 99.9999998% of confidence according to Student law;

σ: the standard deviation.

Solutions complying with the above condition have been further analysed as described in the following section.

h) Expert Validation of the Virtual Hits

A final visual inspection using Selnergy was carried out by visual inspection to discard putative "false positives"—e.g. too constrained conformations, unreasonable interaction patterns etc.—that were not detected by the software. This was carried out for both ligand- and protein-based approaches. At the end of these inspections, the following ranking was obtained:

valid: mode of interaction of the studied molecule similar to the reference ligand (co-crystallised molecule) and/or reference ligand pharmacophore features;

likely: different but plausible modes of interaction of the studied molecule compared to the reference ligand (co-crystallised molecule);

rejected: unlikely mode of interaction and no common pharmacophore compared to compared to the reference ligand.

i) Result—Prediction of Activity of Maclurin and Iriflophenone

The method used is an inverse docking allowing identifying the potential receptor/proteins able to interact with the both molecules using a prediction based on structural homology with known molecules in a data basis. A score over 7 is considered as significant and robust to consider this interaction as possible.

Various proteins involved in the modulation of lipogenesis have been identified, such as PPAR family or Retinoic family, which are very well-known to control the sebum production at transcriptomic level.

Additionally, it was demonstrated that iriflophenone can interact directly with enzymes involved in the sebum production such as FDA synthase, Squalene synthase and others. These results suggested that iriflophenone could have an impact through a transcriptomic control playing on PPAR family or directly by interacting with enzymes related to sebum production.

Similar results were obtained with maclurin, suggesting a potential control of lipogenesis through PPAR and Retinoic family and by a direct interaction with some enzymes involved in sebum production.

The results are summarised in the following tables.

TABLE 14

| Iriflophenon | | | |
|---|---|---|---|
| Category | Name | Score | Consequence |
| Transcription factor/receptor | PPARγ | 9.4758 | Modulation of lipogenesis |
| | PPARα | 7.0902 | |
| | PPARδ | 7.0194 | |
| | Retinoic acid receptor β | 7.6238 | |
| | Insulin receptor | 7.3242 | |
| | RXR α | 7.1998 | |
| Enzyme | FAD synthetase | 8.4401 | Direct impact on specific proteins of sebum |
| | Squalene synthase | 8.5685 | |
| | Cholesterol oxidase | 8.3317 | |
| | Farnesyl pyrophosphate synthase | 9.0946 | |
| | Farnesyltransferase/geranylgeranyltransferase type-1 subunit alpha | 7.7084 | |

TABLE 14-continued

| Iriflophenon | | | |
|---|---|---|---|
| Category | Name | Score | Consequence |
| | Farnesyltransferase, CAAX box, alpha | 7.4005 | |

TABLE 15

| Maclurin | | | |
|---|---|---|---|
| Category | Name | Score | Consequence |
| Transcription factor/receptor | RXR alpha | 8.9948/7.1674 | Modulation of lipogenesis |
| | Nuclear receptor ROR-alpha | 7.1393 | |
| | Glucocorticoid receptor | 7.4371 | |
| | Insulin receptor | 7.7369 | |
| | IGF1 | 8.7891 | |
| | PPARγ | 7.7828 | |
| | PPARδ | 7.275 | |
| Enzyme | Farnesyl pyrophosphate synthase | 10.7054 | Direct impact on specific proteins of sebum |
| | FAD synthetase | 7.5232 | |
| | Cholesterol oxidase | 7.5104 | |
| | Fatty acid oxidation complex subunit alpha | 7.0973 | |
| | Squalene synthase | 7.0912 | |

Example 16. Metagenomic Analysis a) Microbiota Sampling and Storage

Skin microbiota of the panel described in Example 12a) was also studied during the same clinical evaluation. Samples of microflora were collected from the forehead of 40 volunteers by a non-invasive swabbing method, using sterile swabs moistened with a sterile solution of 0.15 M NaCl. Swabs were transferred at −20° C. and kept frozen until DNA extraction. Sampling was done before treatment (D0), and after 28 (D28) days of treatment, using a standardized procedure.

b) DNA Extraction

DNA extraction was performed as described in example 10b.

c) Sequencing and Data Analysis

Sequencing and data analysis was performed as described in example 10c.

d) Results—the Skin Microbiota Composition of African Skins

At the genus level, African skins present the same major genera as Caucasian skin: the *Cutibacterium* and *Staphylococcus* genera (FIG. 25). Further investigations are on-going to identify the major differences between the microbiota compositions of these two ethnicities.

e) Results—*Mangifera indica* Extract Protects the Skin Microbiome of African Skins The placebo disturbs the skin microbiota composition of African skins. Significant modifications generated by the placebo application on the skin microbiota composition have been assessed at the genus level D28. Significant modifications are defined by an adjusted pvalue<0.05, with a proportion higher than 0.01% at, at least, one timepoint.

Between D0 and D28, the proportions of 21 genera are significantly modified by the application of the placebo. Table 16 is summarizing the Genera with proportions significantly impacted between D0 and D28 with relative abundances at each time point and corresponding adjusted pvalues (padj).

TABLE 16

| | D 0 abundance | D 28 abundance | padj (between D 0 and D 28) |
|---|---|---|---|
| *Methylobacterium-Methylorubrum* | 0.04941085 | 0.24454313 | 0.01139 |
| *Sphingomonas* | 0.17602001 | 0.24929342 | 0.00011 |
| *Kingella* | 0.05017204 | 0.06273262 | 0.03534 |
| *Leptotrichia* | 0.15544571 | 0.16188007 | 0.04467 |
| *Moraxella* | 0.28987632 | 0.11059794 | 0.03066 |
| *Paracoccus* | 0.27155502 | 0.06089764 | 0.00407 |
| *Ornithinimicrobium* | 0.02986185 | 0.00631813 | 0.02036 |
| *Rubellimicrobium* | 0.06036825 | 0.00833015 | 0.01001 |
| *Marmoricola* | 0.08328891 | 0.00854412 | 0.02036 |
| *Pseudonocardia* | 0.01564597 | 0.00143435 | 0.02036 |
| *Noviherbaspirillum* | 0.01686238 | 0.00145567 | 0.01854 |
| *Nocardioides* | 0.12592408 | 0.01083437 | 0.00004 |
| *Deinococcus* | 0.08096985 | 0.00635539 | 0.00042 |
| *Blastococcus* | 0.13714 | 0.01063859 | 0.00006 |
| *Microvirga* | 0.04225999 | 0.00321431 | 0.00773 |
| *Flavisolibacter* | 0.04300938 | 0.00306361 | 0.02299 |
| *Modestobacter* | 0.02900026 | 0.00131883 | 0.01257 |
| *Rubrobacter* | 0.0570926 | 0.00222807 | 0.00454 |
| *Solirubrobacter* | 0.02249071 | 0.000824 | 0.02441 |
| *Craurococcus-Caldovatus* | 0.02398628 | 0.00081005 | 0.01350 |
| *Hymenobacter* | 0.05715921 | 0.00134035 | 0.00774 |

Figure 27:
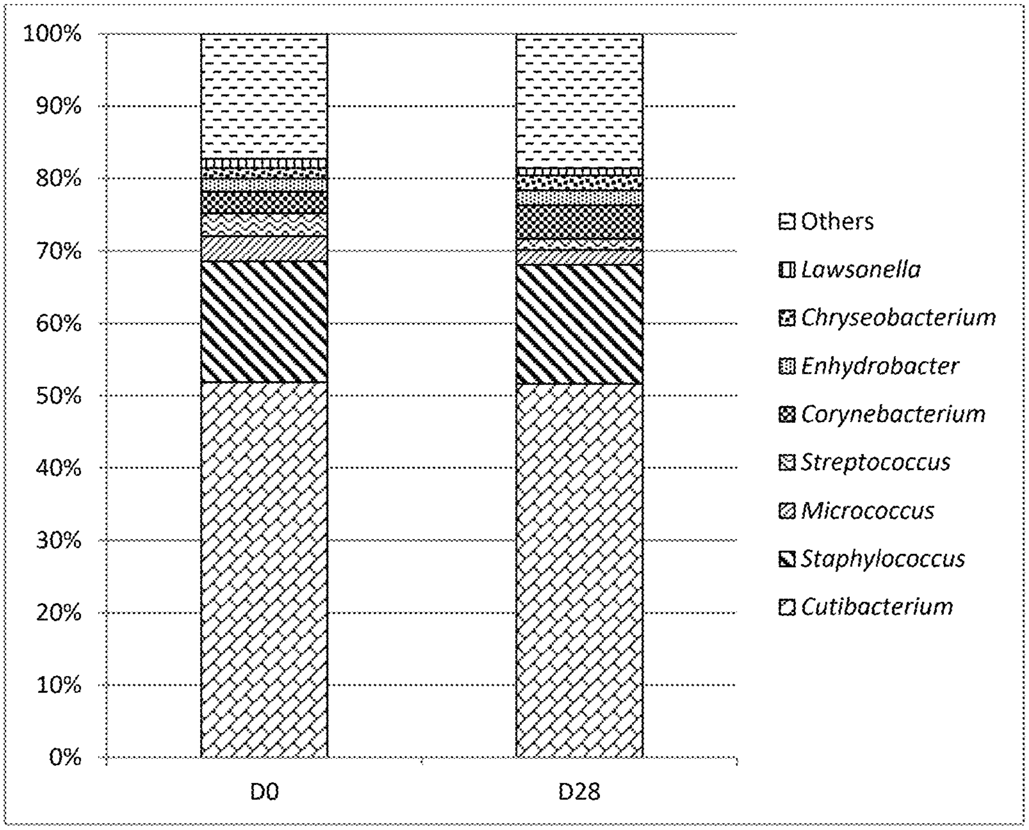
FIG. 27 shows that the major genera in Table 16 are not impacted by the application of the placebo.

The evolution of these genera impacted by the application of the placebo during 28 days on African skins is summarized in FIG. 26. The major genera are not impacted by the application of the placebo, as apparent from FIG. 27.

Significant modifications generated by the *Mangifera indica* extract application on the skin microbiota composition have been assessed at the genus level at D28. Significant modifications are defined by an adjusted pvalue<0.05, with a proportion higher than 0.01% at, at least, one time point.

Figure 28:
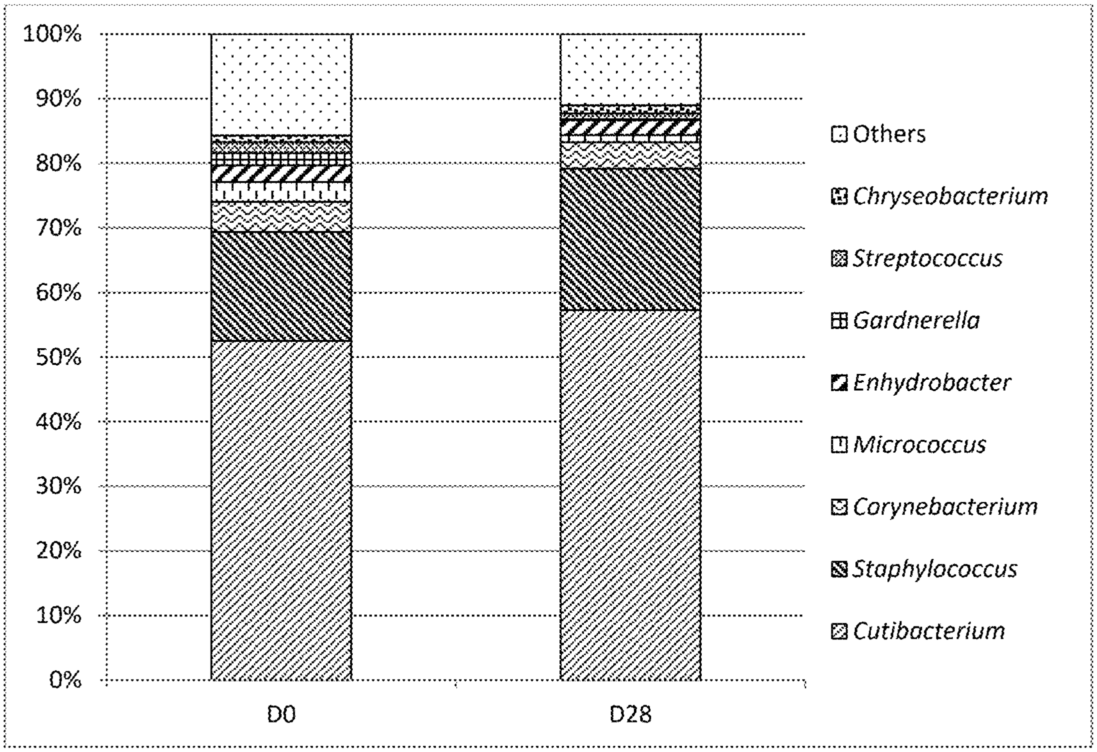
FIG. 28 shows that between D0 and D28, the proportion of one genus is significantly modified by the application of the *Mangifera indica* extract: the Novosphingobium genus. None of the major genus is modified.

Between D0 and D28, the proportion of one genus is significantly modified by the application of the *Mangifera indica* extract: the Novosphingobium genus (padj=0.0017; with a proportion of 0.016% of the skin microbiota at D0 and 0.0004% at D28). None of the major genus is modified (FIG. 28).

f) Conclusion

The application of the placebo involves a major disturbance on the microbiota of African skins at D28, with the significant modulation of 21 genera proportions, representing 1.82% of the global microbiome composition.

In contrary, when the placebo is supplemented with *Mangifera indica* extract, the skin microbiota remains stable after 28 days of application, with the only modification of the proportion of one minor genus, representing 0.016% of the global microbiome composition.

These results indicate the *Mangifera indica* extract enable to protect the microbiome of African skins.

Example 17. Lipase Activity of Severe Acne *C. acnes* Phylotype a) Culture Growth Severe acne *C. acnes* phylotype (IA1, ARCC 6919) was cultured in reinforced clostridial broth as recommended by ATCC at 25° C. pH was adjusted at 6.8+/−0.2. The bacteria were incubated for 2 days at these conditions in order to initiate the growth. During the exponential phase, triolein (used as lipase substrate) was added at 1% to the cultures, one of which was treated with *Mangifera indica* extract at 2% (Sample B), while the other one was untreated (Sample A). After 2 days of incubation, the colonies were counted and quantified for both samples.

b) Sample Treatment and Analysis

The medium of each condition was collected in order to identify and quantify the lipids present at the end of culture. The tubes containing the samples were thawed at ambient temperature then centrifuged for 5 min at 20 000 g at 4° C. The liquid was then collected and place into a new tube. 1 ml of purified water and 3 ml of chloroform/methanol mixture was added. The mixture was stirred at room temperature for 1 hour then centrifuged for 5 min at 3500 rpm. The aqueous superior phase was collected and placed into a new tube. 2 mL of chloroform was added and the mixture was stirred for 10 min at room temperature then centrifuged again for 5 min at 3500 rpm. The organic inferior phase was collected and pooled with the previous organic phase. The organic phases were then evaporated until dryness under nitrogen at 50° C. and dissolved into chloroform/methanol mixture. The samples were finally diluted for analysis.

Oleic acid was the product of lipase activity of *C. acnes*. The oleic acid quantification was realized with a GC system (7890A from Agilent) coupled with a MS system (5975C Inert XL EI/CI MSD from Agilent).

c) Results

The previous data evidenced that *Mangifera indica* extract doesn't impact the abundance of *C. acnes* but the analysis of TG/FFA ratio on the sebum suggests a potential impact on.

It is known that the conversion of TG to FFA is managed by lipases from *C. acnes*. The level of lipase activity is involved in the virulence of *C. acnes*. The phylotypes related to acne skin have a higher lipase activity than phylotypes related to healthy skins (Lee at al., 2019 and Kim et al., 2020).

A phylotype of *C. acnes* coming from severe acne skin was used to measure the lipase activity (phylotype IA1), to show if *Mangifera indica* extract can modulated the *C. acnes* metabolism by reducing the lipase activity The lipase activity is measured by the conversion of triolein into oleic acid in presence or absence of *Mangifera indica* extract at 2%.

Figure 29:
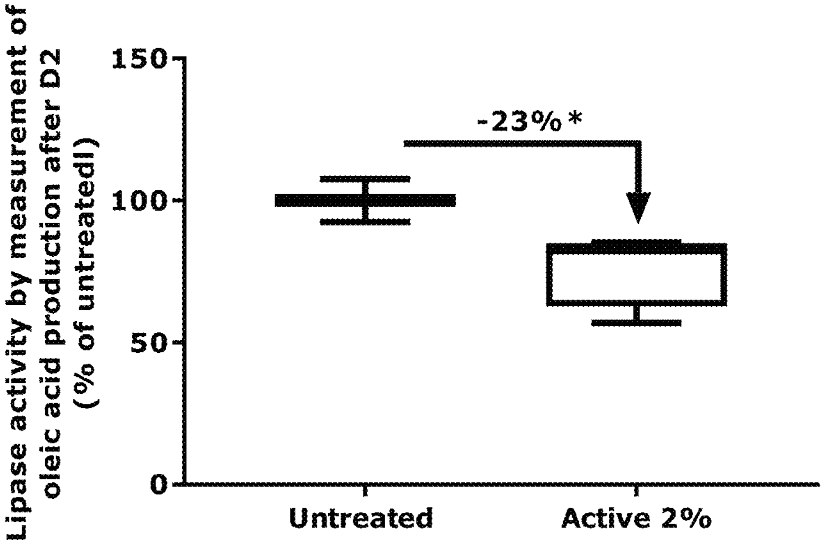
FIG. 29 shows that the presence of *Mangifera indica* extract at 2% reduced the lipase activity on *C. acnes* severe acne phylotype by −23%.

The presence of *Mangifera indica* extract at 2% reduced the lipase activity on *C. acnes* severe acne phylotype by −23% (FIG. 29). This results explained how *Mangifera indica* extract is able to be microbiota friendly and improves the sebum quality by controlling *C. acnes* metabolism which are both favourable to prevent acne.

The invention claimed is:

1. A method of utilizing an extract comprising *Mangifera indica* leaves in skin care for reduction of sebum production and/or reduction of the volume of the sebaceous glands and/or improvement of sebum quality, wherein the extract is provided in a mixture of propanediol and water as carrier solvent, wherein the mixture of propanediol and water is used as extraction solvent, and wherein the ratio of propanediol and water is in the range between 1:1 and 5:1.

2. The method of claim 1, wherein the ratio of propanediol and water is in the range between 2:1 and 4:1.

3. The method of claim 2, wherein the ratio of propanediol and water is 3:1.

4. A method of regulating the sebum production by applying a cosmetic composition comprising a carrier and at least an extract comprising *Mangifera indica* leaves as an active ingredient to human skin or scalp, wherein the extract is provided in a mixture of propanediol and water as carrier solvent, wherein the mixture of propanediol and water is used as extraction solvent, and wherein the ratio of propanediol and water is in the range between 1:1 and 5:1.

5. The method of claim 4, wherein the ratio of propanediol and water is in the range between 2:1 and 4:1.

6. The method of claim 5, wherein the ratio of propanediol and water is 3:1.

7. A method of utilizing an extract comprising *Mangifera indica* leaves in skin care for improvement of acne conditions, wherein the extract is provided in a mixture of propanediol and water as carrier solvent, wherein the mixture of propanediol and water is used as extraction solvent, and wherein the ratio of propanediol and water is in the range between 1:1 and 5:1.

8. The method of claim 7, wherein the ratio of propanediol and water is in the range between 2:1 and 4:1.

9. The method of claim 8, wherein the ratio of propanediol and water is 3:1.

10. A method of utilizing an extract comprising *Mangifera indica* leaves in skin care for reduction of porphyrin intensity, wherein the extract is provided in a mixture of propanediol and water as carrier solvent, wherein the mixture of propanediol and water is used as extraction solvent, and wherein the ratio of propanediol and water is in the range between 1:1 and 5:1.

11. The method of claim 10, wherein the ratio of propanediol and water is in the range between 2:1 and 4:1.

12. The method of claim 11, wherein the ratio of propanediol and water is 3:1.

13. A method of utilizing an extract comprising *Mangifera indica* leaves in skin care for improvement of skin barrier, wherein the extract is provided in a mixture of propanediol and water as carrier solvent, wherein the mixture of propanediol and water is used as extraction solvent, and wherein the ratio of propanediol and water is in the range between 1:1 and 5:1.

14. The method of claim 13, wherein the ratio of propanediol and water is in the range between 2:1 and 4:1.

15. The method of claim 14, wherein the ratio of propanediol and water is 3:1.

16. A method of utilizing an extract comprising *Mangifera indica* leaves in skin care for prevention of dry skin, wherein the extract is provided in a mixture of propanediol and water as carrier solvent, wherein the mixture of propanediol and water is used as extraction solvent, and wherein the ratio of propanediol and water is in the range between 1:1 and 5:1.

17. The method of claim 16, wherein the ratio of propanediol and water is in the range between 2:1 and 4:1.

18. The method of claim 17, wherein the ratio of propanediol and water is 3:1.

19. A method of utilizing an extract comprising *Mangifera indica* leaves in skin care for micro balancing effect on acneic phylotype of *P. acnes* (IA1), wherein the extract is provided in a mixture of propanediol and water as carrier solvent, wherein the mixture of propanediol and water is used as extraction solvent, and wherein the ratio of propanediol and water is in the range between 1:1 and 5:1.

20. The method of claim 19, wherein the ratio of propanediol and water is in the range between 2:1 and 4:1.

21. The method of claim 20, wherein the ratio of propanediol and water is 3:1.

* * * * *